United States Patent [19]

Shepherd

[11] 4,230,878

[45] Oct. 28, 1980

[54] HYPOLIPIDEMIC AND ANTIATHEROSCLEROTIC 4-[(CYCLOPROPYL ALKYL)AMINO]BENZOIC ACIDS AND DERIVATIVES

[75] Inventor: Robert G. Shepherd, South Nyack, N.Y.

[73] Assignee: American Cyanamid Company, Stamford, Conn.

[21] Appl. No.: 884,673

[22] Filed: Mar. 8, 1978

[51] Int. Cl.$^3$ .................. C07C 101/62; C07C 101/60
[52] U.S. Cl. .................................. 560/48; 260/326.85; 260/558 A; 544/93; 544/172; 544/385; 424/310; 424/319; 546/228; 546/294; 548/343; 549/71; 560/19; 562/457; 562/458
[58] Field of Search .................. 562/458, 457; 560/19, 560/48

[56] References Cited

U.S. PATENT DOCUMENTS

| | | | |
|---|---|---|---|
| 3,061,630 | 10/1962 | Pawloski | 562/458 X |
| 3,787,478 | 1/1974 | Dolejs et al. | 560/47 |
| 3,803,211 | 4/1974 | Dolejs et al. | 560/19 |
| 3,868,416 | 2/1975 | Albright et al. | 562/458 |

FOREIGN PATENT DOCUMENTS

| | | |
|---|---|---|
| 2128314 | 1/1972 | Fed. Rep. of Germany . |
| 2338819 | 2/1974 | Fed. Rep. of Germany . |
| 2246267 | 5/1975 | France . |
| 2340726 | 9/1976 | France . |
| 2303534 | 10/1976 | France . |

*Primary Examiner*—Natalie Trousof
*Assistant Examiner*—Vera C. Clarke
*Attorney, Agent, or Firm*—Robert P. Raymond

[57] ABSTRACT

This disclosure describes 4-[(unsaturated or cyclopropylated alkyl)amino]benzoic acids and derivatives useful as hypolipidemic and antiatherosclerotic agents.

6 Claims, No Drawings

HYPOLIPIDEMIC AND ANTIATHEROSCLEROTIC 4-[(CYCLOPROPYL ALKYL)AMINO]BENZOIC ACIDS AND DERIVATIVES

BRIEF SUMMARY OF THE INVENTION

This invention relates to new organic compounds and more particularly, is concerned with novel 4-(alkenylamino, cyclopropylalkylamino, and alkynylamino)benzoic acids and derivatives which may be represented by the following structural formula:

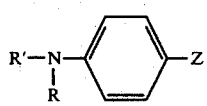

I wherein R' is a branched ur unbranched mono- or polyunsaturated or cyclopropylated $C_3$-$C_{22}$ alkyl group and can be represented by the formula:

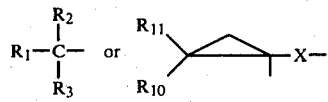

wherein $R_2$ and $R_3$ are the same or different and are hydrogen or a saturated or unsaturated $C_1$ to $C_9$ alkyl group;

Z is a moiety of the formula:

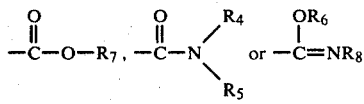

wherein $R_7$ is hydrogen; a loweralkyl group unsubstituted or substituted with one or more moieties selected from the group consisting of hydroxy, carboxyl, carboloweralkoxy, carboxamido, N,N-diloweralkylcarboxamido, cyano, diloweralkylamino, piperazino or polymethyleneimino (ring size 5-8) group; a benzyl group unsubstituted or substituted with at least one halogen or carboxy group; a phenyl moiety unsubstituted or substituted with at least one halogen, carboxyl, carboloweralkoxy, loweralkyl, carboxamido, loweralkoxy or cyano group; or a 3-pyridyl group unsubstituted or substituted with a loweralkyl group, halogen, cyano, carboxyl, carboloweralkoxy, loweralkoxy hydroxy group;

$R_4$ is selected from the group consisting of hydrogen, carboxyloweralkyl, carboalkoxyloweralkyl, loweralkanoyl, loweralkanesulfonyl, arylsulfonyl, sodium sulfo loweralkyl, sulfo loweralkyl, loweralkenyl, loweralkynyl, phenylloweralkyl and ω-hydroxyloweralkyl; $R_5$ is selected from the group consisting of hydrogen, loweralkyl, hydroxy, loweralkoxy, haloloweralkyl, phenyl, carboxyphenyl, chlorophenyl, sodium sulfophenyl, pyridyl, pyridyl loweralkyl, (mono- and polyhydroxyl)-lower alkyl,ω-loweralkoxyloweralkyl; ω-di(-loweralkyl)aminoloweralkyl, ω-piperidinoloweralkyl, ω-pyrrolidinohydroxyloweralkyl, amino, loweralkanoylamino, loweralkanesulfonylamino, N-piperidyl, arylsulfonylamino, and 4-loweralkyl-1-piperazino; $R_4$ and $R_5$ taken together with the associated nitrogen is selected from the group consisting of pyrrolidino, piperidino, morpholino, hexamethyleneimino, 4-(Loweralkyl)piperidino, 4-loweralkyl-1-piperazino, 4-phenylpiperazino, 3-pyrrolinyl, $\Delta^3$-piperidino, 4-(carboethoxy or carboxy)-3-thiazolidinyl and 4-(carboethoxy)-3-oxazolidinyl; $R_6$ and $R_8$ are the same or different and are selected from the group consisting of loweralkyl, (mono- and polyhydroxy)loweralkyl, carboxyloweralkyl, sulfo loweralkyl, sodium sulfo loweralkyl, and, when taken together, loweralkylene; R is selected from the group consisting of hydrogen or a group convertible in vivo thereinto, such as, methyl, carboxymethyl, acetyl, succinyl, 1-(sodium sulfo)loweralkyl, 1-(sodium sulfo)-polyhydroxyalkyl and ω-ar-[1,3-bis-(sodium sulfo)]loweralkyl and wherein $R_1$ is a:

Formula I-A) $C_2$ to $C_{21}$ E- or Z-alkenyl group unsubstituted or substituted with at least one loweralkyl group;

Formula I-B) $C_2$ to $C_{20}$ alkynyl group unsubstituted or substituted with at least one methyl or ethyl group;

Formula I-C) $C_4$ to $C_{20}$ alkyl group containing at least 2 non-cumulative double bonds, said group being unsubstituted or substituted with at least one methyl or ethyl group;

Formula I-D) $C_3$ to $C_{12}$ allenyl group unsubstituted or substituted with at least one methyl or ethyl group;

Formula I-E) vinyl or $C_3$ to $C_8$ E- or Z-alkenyl group said vinyl or alkenyl group being unsubstituted or substituted with at least one methyl group, and in this Formula I-E, $R_2$ is a vinyl or $C_3$ to $C_8$ E- or Z-alkenyl group unsubstituted or substituted with at least one methyl group;

Formula I-F) allyl or $C_4$ to $C_8$ E- or Z-alkenyl group said allyl or alkenyl group being substituted with at least one exo-(methylene, ethylidene, or isopropylidene), and either further unsubstituted or substituted with at least one methyl group;

Formula I-G) vinyl or $C_3$ to $C_8$ E- or Z-alkenyl group substituted between the nitrogen and the double bond with at least one loweralkenyl said vinyl or alkenyl group being unsubstituted or substituted with at least one methyl group;

Formula I-H) vinyl $C_3$ to $C_8$ E- or Z-alkenyl group said vinyl or alkenyl group being unsubstituted or substituted with at least one methyl and in this case, $R_2$ is a $C_2$ to $C_9$ alkynyl group unsubstituted or substituted with at least one methyl group;

Formula I-I) $C_4$ to $C_{20}$ alkyl group containing at least one carbon-carbon double bond and at least one carbon-carbon triple bond said group being unsubstituted or substituted with at least one loweralkyl group;

or wherein R' is a:

Formula I-J) group of the formula

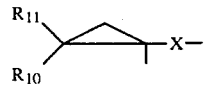

wherein $R_{11}$ is hydrogen or a $C_1$ to $C_{15}$ alkyl group unsubstituted or substituted with at least one methyl group, $R_{10}$ is hydrogen or methyl and X is a bond or a $C_1$ to $C_{15}$ branched or unbranched alkylene group unsubstituted or substituted with at least one methyl group;

and the pharmaceutically acceptable non-toxic aciddaddition and cationic salts thereof.

The loweralkyl, loweralkenyl, loweralkynyl, loweralkoxy, loweralkanoyl, and loweralkanesulfonyl groups referred to herein contain 1 to 6 carbon atoms and are optionally unbranched or branched. The polyhydroxy and polycarboxy groups referred to above contain 2 to 4 hydroxy or carboxy groups, respectively.

Preferred compounds of Formula I, including preferred compounds of Formulas I-A through I-J are described below.

Preferred compounds of Formula I are those wherein Z is:

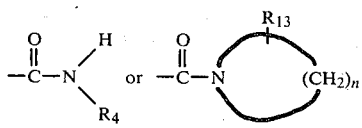

wherein $R_4$ is a loweralkyl group substituted with at least one hydroxyl group, allyl, propargyl, 2-sulfoethyl, —$(CH_2)_m$—$COOR_9$ wherein m is 2–4 and $R_9$ is hydrogen or a loweralkyl group,

wherein $R_{12}$ is a loweralkyl or aryl group, —$SO_2R_{12}$,

or a —$NHSO_2$—$R_{12}$ group; n is one of the integers 4, 5 and 6 and $R_{13}$ is hydrogen or at least one methyl group.

Also preferred are compounds of Formula I wherein Z is the moiety

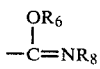

wherein $R_6$ and $R_8$ are as previously defined.

Additionally preferred compounds of Formula I are those where Z is the moiety $COOR_7$, wherein $R_7$ is hydrogen; a loweralkyl group unsubstituted or substituted with one or more carboxyl, hydroxyl, diloweralkylamino or polymethyleneimino (ring size 5–8) groups; a benzyl or phenyl group which is unsubstituted or substituted with at least one halogen or carboxyl group; or 3-pyridyl.

The most preferred compounds of Formula I are those set forth above wherein R is hydrogen, $R_2$ and $R_3$ are hydrogen or methyl.

Preferred compounds of Formula I-A are those as defined above and those wherein $R_1$ is a vinyl or $C_{13}$ to $C_{21}$ E- or Z-alkenyl group said vinyl or alkenyl group being unsubstituted or substituted with at least one methyl group; most preferred compounds of Formula I-A are those wherein $R_1$ is a $C_7$ to $C_{15}$ E- or Z-alkenyl group; and the most preferred of these are those in which R, $R_2$ and $R_3$ are hydrogen and $R_7$ is hydrogen or a loweralkyl bearing either one or two substitutents selected from the group consisting of hydroxy, carboxy, carboethoxy, diloweralkylamino, and 4-methyl-1-piperazino.

Preferred compounds of Formula I-B are those as defined above and those wherein $R_2$ and $R_3$ are methyl; even more preferred compounds of Formula I-B are those wherein $R_1$ is $C_2$ to $C_{18}$ alkynyl and most preferred are those wherein $R_1$ is $C_7$ to $C_{18}$ alkynyl; and the most preferred of these are those wherein R, $R_2$ and $R_3$ are hydrogen and $R_7$ is as defined immediately above.

Preferred compounds of Formula I-C are those as defined above and those wherein $R_2$ and $R_3$ are hydrogen or a loweralkyl group and those compounds of Formula I-C wherein $R_1$ is $C_4$ to $C_{18}$ alkyl group containing at least two non-cumulative double bonds; and most preferred of these are those wherein R, $R_2$ and $R_3$ are hydrogen and $R_7$ is as defined immediately above.

Preferred compounds of Formula I-D are those as defined above and those wherein $R_2$ is methyl; more preferred compounds are those of Formula I-D wherein $R_1$ is a $C_3$ to $C_{12}$ allenyl group and the other groups are as defined above; and the most preferred of these are those wherein R, $R_2$ and $R_3$ are hydrogen and $R_7$ is as defined immediately above.

Preferred compounds of Formula I-E are those as defined above and those wherein $R_1$ is a $C_2$ or $C_3$ alkenyl group; and the most preferred of these are those wherein R, $R_2$ and $R_3$ are hydrogen and $R_7$ is as defined immediately above.

Particularly preferred compounds of Formula I-F are those wherein the substituents are as defined immediately above except that R, $R_2$ and $R_3$ are hydrogen and $R_7$ is as defined immediately above.

Particularly preferred compounds of Formula I-G are those wherein R, $R_2$ and $R_3$ are hydrogen and $R_7$ is as defined immediately above.

Particularly preferred compounds of Formula I-H are those where R, $R_2$ $R_3$ are hydrogen; more preferred compounds are those where $R_1$ is a loweralkenyl or loweralkynyl group; and $R_7$ is a defined immediately above.

Particularly preferred compounds of Formula I-I are those wherein $R_2$ and $R_3$ are the same or different and each is hydrogen or methyl. More preferred compounds of Formula I-I are those wherein $R_3$ and/or $R_2$ is hydrogen; and other preferred compounds of Formula I-I are those wherein $R_1$ is a $C_4$ to $C_{13}$ alkyl group containing at least one carbon-carbon double bond and at least one carbon-carbon triple bond. Most preferred compounds of Formula I-I are those wherein $R_1$ is a $C_6$ to $C_{18}$ alkyl group containing at least one carbon-carbon double bond and at least one carbon-carbon triple bond and $R_7$ is as defined immediately above.

Particularly preferred compounds of Formula I-J are those wherein $R_{10}$ is hydrogen. Most preferred compounds of Formula I-J are those wherein R, and $R_{10}$ are hydrogen and $R_7$ is as defined immediately above.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel 4-[(unsaturated or cyclopropylated alkyl)amino]benzoic acids and derivatives of the present invention. These compounds may be utilized either as such or in the form of a pharmaceutically acceptable salt with an organic or inorganic acid or base. The invention also contemplates a method for lowering serum lipids and for ameliorating atherosclerosis in mammals by the administration of said acids and derivatives.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholestrol is a major component of atherosclerotic lesions or plaques. Investigators have been trying to determine the role of cholesterol in lesion initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon & Verter, 1969) in over 5,000 persons of more than 12 years established a correlation between high concentrations of blood cholesterol and increased risk of heart attack. Although the causes of coronary artery disease are multiple, one of the most constant factors has been the elevated concentration of lipids in blood plasma. A combined elevation of cholesterol and triglycerides has been shown (Carlson & Bottiger, 1972) to carry the highest risk or coronary heart disease. The majority of patients with ischemic heart disease or peripheral vascular disease were found to have hyperlipoproteinemia, involving very low-density and/or low-density lipoproteins (Lewis et al., 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [Levy & Frederickson, Postgraduate Medicine 47, 130 (1970]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually taken them for a number of years.

DETAILED DESCRIPTION OF THE INVENTION

The compounds of this invention are new and novel 4-[(unsaturated or cyclopropylated alkyl)amino]benzoic acids and derivatives of Formula I (including Formulas I-A to I-J) which have useful biological and pharmacological properties. No hypolipidemic activity has been reported in the literature for these compounds and they are different in structure from other hypolipidemic agents. The compounds of this invention lower serum-lipid concentrations and also minimize atheroma formation in the aorta. These substances also provide the oral administration required for hypolipidemic agents, which patients usually take for many years. The novel compounds of this invention are adequately absorbed from the gastrointestinal tract. The 4-(monoalkylamino)benzoic acids and esters were disclosed in U.S. Pat. No. 3,868,416.

We have now found that the compounds of the present invention can safely and effectively lower both serum sterols and triglycerides in warm-blooded mammals. Such actions on serum-lipid components are considered to be very useful in the treatment of atherosclerosis, especially in contrast to available drugs whose action is much more limited. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The novel compounds of the present invention are, in general, white crystalline solids having characteristic melting points are absorption spectra. They are soluble in organic solvents such as lower alkanol, chloroform, benzene, dimethylformamide, and the like, but are generally not very soluble in water. The novel compounds of the present invention, which are organic bases may be converted to their non-toxic acid-addition or cationic salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, ascorbic, and the like. The compounds which contain acidic groups form pharmaceutically acceptable cationic salts with organic or inorganic bases such as the alkali metal hydroxides, the alkaline earth metal hydroxides, and the like. The sodium or potassium salts which are formed in solution in the course of hydrolysis of their esters can be isolated as the solid alkali metal salts by cooling. Where it is desirable to purify a compound in the form of the acid, the salt is conveniently formed by treating its solution with exactly one equivalent of base and evaporation or lyophilization. Alkaline earth salts are prepared similarly, often using their acetate salts as a conveniently soluble form. Organic base salts such as those of N-methylglucamine are prepared by dissolving equimolar mounts of the acid and the base in hot ethanol or aqueous alcohols and cooling to crystallization.

The 4-[(unsaturated or cyclopropylated alkyl)amino]-benzoic acids of this invention are prepared by reaction of loweralkyl 4-aminobenzoates with suitable alkylating agents, such as unsaturated or cyclopropylated alkyl halides, sulfates, tosylates, mesylates or trifluoromethylsulfonates, with or without a solvent at 25°-150° C. Suitable solvents are lower alkanols, chloroform, N,N-dimethylformamide, N,N-dimethylacetamide, diglyme, dimethylsulfoxide, acetonitrile, toluene, benzene, hexamethylphosphoramide and like solvents. The reaction may be carried out with 2 equivalents of the loweralkyl aminobenzoate or with the equivalent of the loweralkyl aminobenzoate and one equivalent of base, such as an unreactive organic base such as diisopropylethylamine or an alkali carbonate or bicarbonate, or with a catalytic amount of copper powder when an appropriate halide is used as the alkylating agent.

The resulting benzoate esters are readily hydrolyzed to the acids in boiling aqueous ethanolic alkali.

The loweralkyl N-acetyl-4-(substituted amino)benzoates are prepared by reaction of a loweralkyl 4-(acetylamino)benzoate with an appropriate unsaturated or cyclopropylated alkyl halide in the presence of an equivalent of sodium hydride in an inert solvent such as N,N-dimethylformamide, N,N-dimethylacetamide or diglyme at 50°-150° C. The N-acetyl benzoate esters are readily hydrolyzed to the acids in boiling aqueous ethanolic dilute alkali or acid.

Alternative methods of preparation are by reductive alkylation of a 4-aminobenzoic ester or amide which may also be generated in situ by reduction of 4-amino precursors such as a 4-nitro group and the like, or by a borohydride reduction of the chloroimide formed with phosphorus oxychloride from 4-(acylamino)benzoate ester. For example, an unsaturated or cyclopropylated aldehyde or ketone plus 4-aminobenzoyl piperidide are reduced under 1-3 atmospheres of hydrogen using a metal catalyst, to form 4-([unsaturated or cyclopropylated alkyl]amino)benzoyl piperidide.

Two types of substitution reactions also yield the compounds of the present invention, namely reaction of esters or amides of 3,4-didehydrobenzoic acid with an (unsaturated or cyclopropylated alkyl)amine (or its alkali metal salt) and amination of 4-fluorobenzoate esters. The former type of reaction is carried out by treating a 4-halo compound such as 4-bromobenzoyl piperidide with the lithium, potassium or sodium salt of an amine (in excess) such as pentadec-4-enylamine in diethyl ether or other aprotic solvent. The latter type comprises reacting pentadec-4-enylamine or the like with 4-fluorobenzoyl piperidide at elevated temperature.

The novel compounds of the present invention may be readily prepared by treating an acid halide, mixed acid anhydride, or activated ester or amide with a hydroxy compound, an amine, or a salt of a carboxamide or sulfonamide. These reactions are preferably carried out in an inert solvent at a temperature of 5°-125° C. for a period of time from about 30 minutes to 18 hours or more. In the case of the acid halide and other acid-forming acylating agents, the reaction is carried out in the presence of an acid scavenger such as diisopropylethylamine, 4-dimethylaminopyridine, pyridine, triethylamine, finely powdered sodium carbonate, and the like. The acid halide and anhydride starting materials may be obtained from the corresponding 4-(monoalkylamino)benzoic acids by methods which are well-known in the art or described herein. However, a protecting group on the arylamino nitrogen is used for best results. The simplest protecting group is provided by protonation of the amine to give an anilinium salt prior to or during formation of the acylating agent. Acylation of this amino group by carefully selected acyl groups such as carbobenzyloxy, carbo-t-butoxy, and trifluoroacetyl provides protection of this group from self-acylation during amide or ester formation. These protecting groups are then removed by catalytic hydrogenation, mild acid treatment and mild alkali treatment, respectively, (Flowsheet A shows an example of the sequence). Activated esters or amides, which are used to synthesize the esters of the present invention, are carboxymethyl, 4-nitrophenyl, N-oxysuccinimide, 1-imidazolyl and the like. In certain cases, treatment of acids or ordinary esters such as methyl or ethyl with an excess of an appropriate hydroxy-containing substrate in the process of a Lewis or mineral acid such as boron trifluoride, sulfuric acid, or hydrochloric acid is sufficient to convert the 4-([unsaturated or cyclopropylated alkyl]amino)benzoic esters or acids to the appropriate esters.

With certain kinds of substrates for ester formation, it is necessary to form the alkali metal or strong organic base salts of the 4-(substituted amino)benzoic acids in order to react them with 2,3-dihydroxypropyl iodide, ethyl chloroacetate and the like. Other esters are prepared from the acids themselves by reaction with diazoalkanes, ethyl diazoacetate or the like.

FLOW SHEET A

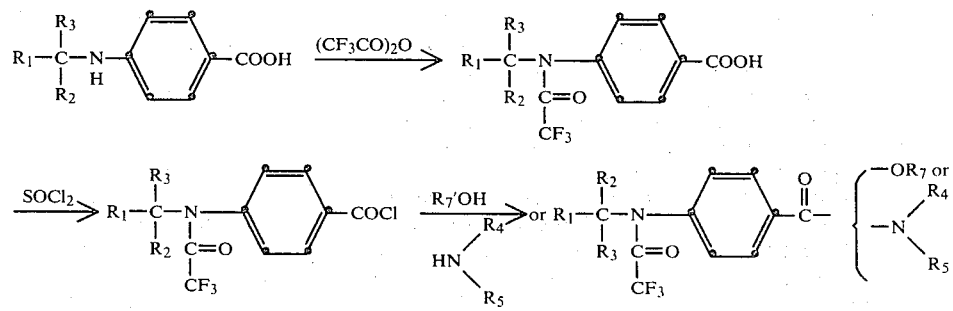

-continued
FLOW SHEET A

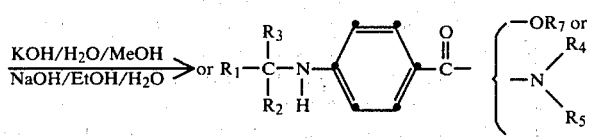

FLOW SHEET B

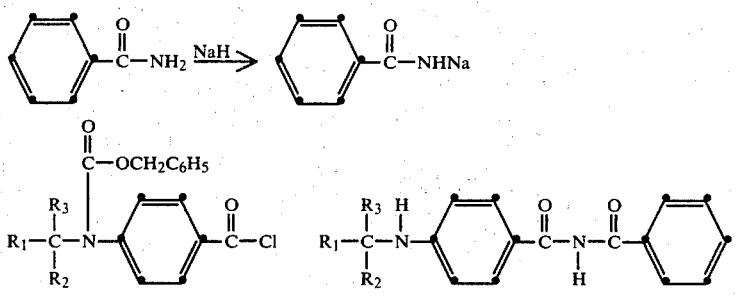

(1) Condensation
(2) Removal of protecting group

The 4-[(unsaturated or cyclopropylated alkyl)amino]-benzoic acids and derivatives are prepared by deacylation of the corresponding 4-(N-trifluoroacetyl-[unsaturated or cyclopropylated alkyl]amino)benzoic ester or amide by reacting with an alkali hydroxide such as sodium or potassium hydroxide in a lower alkanol, water or an aqueous lower alkanol at 5° C. to 50° C. Alternatively, these compounds may be prepared by deacylation of the 4-(N-carbo-t-butoxyalkenylamino)-benzamide and the like with mineral acids such as hydrochloric or hydrobromic acid, preferably in glacial acetic acid at 0° C. to 50° C. Also, they are prepared by removal of the carbobenzyloxy protecting group from the anilino nitrogen atom by means of mild catalytic hydrogenation or by treatment with a mineral acid such as hydrobromic acid in glacial acetic acid.

With certain kinds of substrates for amide formation, it is necessary to form the alkali metal or strong organic base salts of these substrates in order to react them with the various aforementioned acylating forms of the 4-[(unsaturated or cyclopropylated alkyl)amino]benzoic acids. The aminoalkanecarboxylic and aminoalkanesulfonic acids are zwitterionic and must be converted to their cationic salts, suitably in situ. They may also be used in the form of their esters and then hydrolyzed after amide formation. Certain substrates, which are neutral like the carboxamides or slightly acidic like the alkane or arene sulfonamides, are converted to reactive salts by reaction with sodium hydride or other basic reagents, (Flowsheet B is an example of this sequence).

Alternatively the free acids may be prepared by hydrolysis of the corresponding nitriles or various amides, imidates or oxazolines. The carboxylic acid moiety may also be generated by oxidation of the corresponding aldehydes, acetophenones, benzyl alcohols, or toluenes, most often with the use of an amine-protecting group such as trifluoroacetyl or t-butyloxycarbonyl.

Certain derivatives

of the aminobenzoyl nitrogen atom are useful for providing greater solubility, more uniform and reliable intestinal absorption, and for a certain degree of modification of the pharmacology of the compounds of the present invention. Some of these derivatives can be converted to the corresponding N—H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc., in the presence of pyridine, triethylamine or the like at temperatures moderate enough to avoid acylation of the amide moiety. The 1-(sodium sulfo)alkyl derivatives are obtained by reaction of the 4-[(unsaturated or cyclopropylated alkyl)amino]benzoic acid, ester or amide with sodium bisulfite and an aliphatic aldehyde, a polyhydroxyaldehyde such as glyceraldehyde or glucose, or cinnamaldehyde in a mixed organic-aqueous medium. In the case of cinnamaldehyde, the di-sulfonate salts result from addition of the bisulfite to the carbon-nitrogen double bond of the anil intermediate as well as to the carbon-carbon double bond of cinnamaldehyde itself.

The imidates of the present invention are preferably prepared either by addition of hydroxy compounds to the corresponding nitriles or by alkylation of the corresponding amides, suitably bearing a protecting group on the aminobenzoyl nitrogen atom in many cases. The addition of alcohols and other hydroxy compounds is carried out under acid catalysis without additional solvent, if possible. Alkylation of the protonated substituted aminobenzamide may be carried out or the aforementioned aminobenzoyl protecting groups can be employed. In some cases, simultaneous O-alkylation of the amide and N-alkylation of the aminobenzoyl moiety can be used to obtain a desired imidate. Intramolecular formation of imidates results from 2-haloethyl and 3-halopropyl amides as well as from 2-hydroxyethyl and 3-hydroxypropyl amides when treated with a condensing agent.

In certain cases, the unsaturation is introduced at a late stage of the preparation of the 4-(unsaturated alkylamino)benzoic acid derivatives. For example, an alkyl 4-(ω-haloalkylamino)benzoate is dehydrohalogenated to the corresponding olefinic compound or, alternatively, it is converted to a Wittig trialkylphosphonium reagent and reacted with an aldehyde to yield a product with an internal double bond. This ω-halo substrate can also be reacted with an alkylacetylene sodium or lithium salt to form 4-(alkynylamino)benzoic acid derivatives.

The novel compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypocholesteremic and antiatherosclerotic effect than the aforementioned adjuvants and synthetic ingredients. It is not known how these novel compounds operate in the blood serum and no theory of why these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or to otherwise modify the physical form of the dosage unit. For instances, tablets, pills, or capsules may be coated with shellac, sugar or both. A syrup or elixir may contain the active compound, sucrose as a sweetening agent, methyl and propylparabens as preservatives, a dye, and flavoring such as cherry or orange flavor. Of course, any material used in preparing any dosage-unit form should be pharmaceutically pure and substantially non-toxic in the amounts employed. In addition, the active ingredients may be incorporated into sustained-release preparations and formulations.

The invention will be described in greater detail in conjunction with the following specific Examples.

EXAMPLE 1

Preparation of p-(allylamino)benzoic acid; (Method A)

To a solution of 18.2 g. of ethyl p-aminobenzoate in 100 ml. of dimethylformamide is added a solution of 4.7 ml. of allyl bromide in 60 ml. of dimethylformamide. The solution is heated at 60° C. for 5 hours and then cooled and partitioned between diethyl ether and water. The combined ether phases are washed with water, dried over magnesium sulfate, and concentrated in vacuo to provide 16.5 g. of a semi-solid. A portion (6 g.) is absorbed onto 30 g. of silica gel and chromatographed on 475 g. of silica gel to provide the benzoate ester.

A mixture of the ester, 22.0 g. of potassium hydroxide and 200 ml. of ethanol-water (8:1) is stirred under reflux for 6 hours. Concentrated hydrochloric acid (about 80 ml.) is added to the warm mixture and cooling and dilution with water affords a white solid which is collected by filtration and recrystallized from ethanol to yield the product as a white solid.

EXAMPLE 2

Preparation of p-(1-pentadeca-4,14-dienylamino)benzoic acid; (Method B)

To a solution of 4,14-pentadecadien-1-ol (15.0 g.) and triethylamine (14 ml.) in dry methylene chloride (320 ml.) at −8° C. is added methanesulfonylchloride (5.73 ml.), dropwise. The reaction mixture is stirred at −10° C. for 30 minutes and then diluted with methylene chloride, extracted with ice-water (250 ml.), followed by cold 10% hydrochloric acid (200 ml.); cold saturated sodium bicarbonate (200 ml.) and cold brine (200 ml.). The organic phase is dried over magnesium sulfate and the solvent removed in vacuo to provide the crude mesylate.

A solution of 18.1 g. of the above mesylate and 19.8 g. of ethyl p-aminobenzoate in hexamethylphosphoramide is heated at 120° C. for 20 hours. After cooling, the reaction mixture is diluted with 30 ml. of ethanol:water (1:1) (30 ml.) and chilled. More ethanol is added and the solid material is collected. This solid is recrystallized twice from ethanol to provide the benzoate ester.

A mixture of the ester, 22.0 g. of potassium hydroxide and 200 ml. of ethanol-water (8:1) is stirred under reflux for 6 hours. Concentrated hydrochloric acid (about 80 ml.) is added to the warm mixture and cooling and dilution with water affords a white solid which is collected by filtration and recrystallized from ethanol to yield the product as a white solid.

EXAMPLES 3–317

Treatment of the indicated halide or carbinol starting material set forth in Table I below by the indicated method is productive of the product listed in the table. Reference B in Tables I and II is J. Med. Chem. 11, 1190 (1968).

TABLE I

| Example | Starting Material | Method | Product |
|---|---|---|---|
| 3 | E-4-tetradecenol | B | p-(E-1-tetradec-4-enyl-amino)benzoic acid |
| 4 | Z-9-octadecen-1-ol | B | p-(Z-1-octadec-9-enyl-amino)benzoic acid |
| 5 | E-4-pentadecen-1-ol | B | p-(E-1-pentadec-4-enyl-amino)benzoic acid |
| 6 | 3-chloro-2,4,4-trimethyl-1-pentene Chem. Abst. 72, 111081h | A | p-[3-(2,4,4-trimethyl)-pent-1-enylamino]-benzoic acid |
| 7 | 3-bromo-3-isopropyl-4-methyl-1-pentene Chem. Abst. 54, 4355a | A | p-[3-(3-isopropyl-4-methyl)-pent-1-enyl-amino]benzoic acid |
| 8 | 4-bromo-2-heptene Chem. Abst. 70, 67482x | A | p-(4-hept-2-enylamino)-benzoic acid |
| 9 | 4-bromo-2,4-dimethyl-2-hexene | A | p-[4-(2,4-dimethylhex-2-enyl)amino]benzoic acid |
| 10 | 5-chloro-3,5-dimethyl-3-heptene Chem. Abst. 54, 1256e | A | p-[5-(3,5-dimethyl-hept-3-enyl)amino]-benzoic acid |
| 11 | Z-1-hydroxy-2-hexadecene Ref. B | B | p-(Z-1-hexadec-2-enyl-amino)benzoic acid |
| 12 | E-1-hydroxy-2-hexadecene Ref. B | B | p-(E-1-hexadec-2-enyl-amino)benzoic acid |
| 13 | 1-bromo-4-methyl-3-heptene Chem. Abst. 71, 102020q | A | p-[1-(4-methylhept-3-enyl)amino]benzoic acid |
| 14 | 1-bromo-4-methyl-3-nonene Chem. Abst. 71, 101399h | A | p-[1-(4-methylnon-3-enyl)amino]benzoic acid |
| 15 | E-7-bromo-3-heptene Chem. Abst. 74, 99419f | A | p-(1-hept-4-enylamino)-benzoic acid |
| 16 | 1-bromo-5,9-dimethyl-4-decene Chem. Abst. 51, 8699g | A | p-[1-(5,9-dimethyl-dec-4-enyl)amino]-benzoic acid |
| 17 | 1-methanesulfonyl-oxy-4-tetradecene Ref. B. | B | p-(1-tetradec-4-enyl-amino)benzoic acid |
| 18 | 1-methanesulfonyl-oxy-4-hexadecene Ref. B. | B | p-(1-hexadec-4-enyl-amino)benzoic acid |
| 19 | 6-bromo-1-hexene Chem. Abst. 66, 2142j | A | p-(1-hex-5-enyl-amino)benzoic acid |
| 20 | 6-bromo-2-methyl-1-hexene Chem. Abst. 75, 109624f | A | p-[1-(5-methylhex-5-enyl)amino]benzoic acid |
| 21 | 6-chloro-1-heptene Chem. Abst. 72, 31877q | A | p-(2-hept-6-enylamino)-benzoic acid |
| 22 | 6-bromo-2-methyl-2-heptene Chem. Abst. 54, 13166f | A | p-[2-(2,6-dimethyl-hept-5-enyl)amino]-benzoic acid |
| 23 | 7-chloro-2-octene Chem. Abst. 75, 129245m | A | p-(2-oct-6-enylamino)-benzoic acid |
| 24 | E-1-chloro-4-nonene Chem. Abst. 67, 32294g | A | p-(E-1-non-5-enyl-amino)benzoic acid |
| 25 | 7-bromo-1-heptene | A | p-(1-hept-6-enyl-amino)benzoic acid |
| 26 | 7-chloro-1-octene Chem. Abst. 75, 29245m | A | p-(2-oct-7-enylamino)-benzoic acid |
| 27 | 6-bromo-6-methyl-1-heptene Chem. Abst. 66, 94482w | A | p-[1-(2-methylhept-6-enyl)amino]benzoic acid |
| 28 | 6-chloro-6-methyl-1-heptene Chem. Abst. 75, 129245 | A | p-([1-(6-methylhept-6-enyl)amino]benzoic acid |
| 29 | E-8-bromo-2-octene Chem. Abst. 74, 99419f | A | p-(1-oct-6-enylamino)-benzoic acid |
| 30 | 8-bromo-2,6-dimethyl-2-octene Chem. Abst. 72, 90573c | A | p-[(1-(3,7-dimethyl-oct-6-enyl)amino]-benzoic acid |
| 31 | 11-bromo-5-undecene-Chem. Abst. 67, 73101b | A | p-(1-undec-6-enyl-amino)benzoic acid |
| 32 | 8-bromo-1-octene Chem. Abst. 70, 10990g | A | p-(1-oct-7-enylamino)-benzoic acid |
| 33 | R-8-iodo-7-methyl-1-octene Chem. Abst. 74, 12573e | A | p-[R-(2-methyloct-7-enyl)amino]benzoic acid |
| 34 | 1-chloro-7-tetra-decene Chem Abst. 54, 22461h | A | p-(1-tetradec-7-enyl-amino)benzoic acid |
| 35 | 9-chloro-1-nonene Chem. Abst. 70 114490k | A | p-(1-non-8-enylamino)-benzoic acid |
| 36 | 1-bromo-8-hepta-decene Chem. Abst. 52, 249d | A | p-(1-heptadec-8-enyl-amino)benzoic acid |
| 37 | E-1-bromo-9-octadecene Chem. Abst. 70, 46779j | A | p-(E-1-octadec-9-enyl-amino)benzoic acid |
| 38 | Z-1-bromo-9-octadecene Chem. Abst. 70, 46779j | A | p-(Z-1-octadec-9-enyl-amino)benzoic acid |
| 39 | 11-chloro-1-undec-ene Chem. Abst. 66, P19046d | A | p-(1-undec-10-enyl-amino)benzoic acid |
| 40 | 12-iodo-3,7,11-trimethyl 1-dodecene | A | p-[1-(2,6,10-trimethyl-dodec-11-enyl)amino]-benzoic acid |
| 41 | 13-bromo-1-tridec-ene Chem. Abst. 67, 43348v | A | p-(1-tridec-12-enyl-amino)benzoic acid |
| 42 | 22-bromo-9-docos-ene Chem. Abst. 73, 44976j | A | p-[1-(2-methylhept-6-enyl)amino]benzoic acid |
| 43 | 16-methanesulfonyl-oxy-1-decene Ref. B | B | p-(1-hexadec-15-enyl-amino)benzoic acid |
| 44 | propargyl alcohol | B | p-(1-prop-2-ynyl-amino)benzoic acid |
| 45 | 3-chloro-1-butyne | A | p-(2-but-3-ynylamino)-benzoic acid |
| 46 | 3-chloro-3-methyl-nonyne Chem. Abst. 55, 22090i | A | p-[3-(3-methylnon-1-ynyl)amino]benzoic acid |
| 47 | 3-bromo-1-penta-decyne Chem. Abst. 53, 21638c | A | p-(3-pentadec-1-ynyl-amino)benzoic acid |
| 48 | 1-octyn-3-ol Chem. Abst. 66, 85410n | B | p-(3-oct-1-ynylamino)-benzoic acid |
| 49 | 3,7,11,15-tetramethyl-1-hexadecyn-3-ol | B | p-[3-(3,7,11,15-tetra-methylhexadec-1-ynyl)-aminobenzoate |
| 50 | 2-butyn-1-ol | B | p-(1-but-2-ynylamino)-benzoic acid |
| 51 | 4-hexyn-3-ol | B | p-(3-hex-4-ynylamino)-benzoic acid |
| 52 | 2-methyl-3-pentyn-2-ol Chem. Abst. 69, 10496e | B | p-[2-(2-methylpent-3-ynyl)amino]benzoic acid |

TABLE I-continued

| Example | Starting Material | Method | Product |
|---|---|---|---|
| 53 | 2-octyn-1-ol | B | p-(1-oct-3-ynylamino)benzoic acid |
| 54 | 4-decyn-3-ol Chem. Abst. 69, P4630s | B | p-(3-dec-4-ynylamino)benzoic acid |
| 55 | 1-bromo-2-dodecyne Chem. Abst. 28, 40345 | A | p-[1-dodec-2-ynylmino)benzoic acid |
| 56 | 1-methanesulfonyloxy-2-pentadecyne J. Med. Chem 19, 946 (1977) | B | p-(1-pentadec-2-ynylamino)benzoic acid |
| 57 | 3-butyne-1-ol Chem. Abst. 66, P2319a | B | p-(1-but-3-ynylamino)benzoic acid |
| 58 | 1-undecyn-4-ol Chem. Abst. 70, 3219j | B | p-(4-undec-1-ynylamino)benzoic acid |
| 59 | 2-methyl-4-pentyn-2-ol Chem. Abst. 68, 12200g | B | p-[2-(2-methylpent-4-ynyl)amino]benzoic acid |
| 60 | 4-pentyn-2-ol Chem. Abst. 64, 13537e | B | p-(2-pent-4-ynylamino)benzoic acid |
| 61 | 3-pentyn-1-ol | B | p-(1-pent-3-ynylamino)benzoic acid |
| 62 | 4-hexyn-2-ol | B | p-(2-hex-4-ynylamino)benzoic acid |
| 63 | 2-methyl-3-pentyn-1-ol Chem. Abst. 66, 115242k | B | p-[1-(2-methyl-3-pent-3-ynyl)amino]benzoic acid |
| 64 | 2-(1-propynyl)-1-heptanol Chem. Abst. 66, 115242k | B | p-[1-2-(1-propynyl-heptyl)amino]benzoic acid |
| 65 | 2-methyl-4-nonyn-2-ol Chem. Abst. 68, 104593r | B | p-[2-(2-methylnon-4-ynyl)amino]benzoic acid |
| 66 | 2-methyl-3-nonyn-1-ol Chem. Abst. 66, 115242k | B | p-[1-(2-methylnon-3-ynyl)amino]benzoic acid |
| 67 | 3-nonyn-1-ol Chem. Abst. 75, 5165r | B | p-(1-non-3-ynylamino)benzoic acid |
| 68 | 2-methyl-3-decyn-1-ol Chem. Abst. 66, 115242k | B | p-[1-(2-methyldec-3-ynyl)amino]benzoic acid |
| 69 | 5-chloro-1-pentyne | A | p-(1-pent-4-ynylamino)benzoic acid |
| 70 | 4-hexyn-1-ol Chem. Abst. 74, 9800w | B | p-(1-hex-4-ynylamino)benzoic acid |
| 71 | 1-chloro-4-nonyne | A | p-(1-non-4-ynylamino)benzoic acid |
| 72 | 1-chloro-4-tridecyne Chem. Abst. 32, 7426³ | A | p-(1-pentadec-2-ynylamino)benzoic acid |
| 73 | 1-chloro-4-hexadecyne | A | p-(1-hexadec-4-ynylamino)benzoic acid |
| 74 | 5-hexyn-1-ol Chem. Abst. 74, 9800w | B | p-(1-hex-5-ynylamino)benzoic acid |
| 75 | 6-octyn-2-ol Chem. Abst. 71, 60300y | B | p-[2-(2-methyloct-6-ynyl)amino]benzoic acid |
| 76 | 1-iodo-5-decyne Chem. Abst. 51, 12817f | A | p-(1-dec-5-ynylamino)benzoic acid |
| 77 | 5-tetradecyn-1-ol Chem. Abst. 71, 120523k | B | p-(1-tetradec-5-ynylamino)benzoic acid |
| 78 | 5-octadecyn-1-ol Chem. Abst. 72, 42686v | B | p-(1-octadec-5-ynylamino)benzoic acid |
| 79 | 6-octadecyn-1-ol Chem. Abst. 72, 42686v | B | p-(1-octadec-6-ynylamino)benzoic acid |
| 80 | 10-chloro-3-decyne Chem. Abst. 67, 108147a | A | p-(1-dec-7-ynylamino)benzoic acid |
| 81 | 1-chloro-7-tetradecyne Chem. Abst. 54, 22461e | A | p-(1-tetradec-7-ynylamino)benzoic acid |
| 82 | 7-hexadecyn-1-ol Chem. Abst. 71, 19554w | B | p-(1-hexadec-7-ynylamino)benzoic acid |
| 83 | 7-octadecyn-1-ol Chem. Abst. 67, 81784w | B | p-(1-octadec-7-ynylamino)benzoic acid |
| 84 | 8-octadecyn-1-ol Chem. Abst. 72, 42686v | B | p-(1-octadec-8-ynylamino)benzoic acid |
| 85 | 9-decyn-1-ol Chem. Abst. 67, 81784s | B | p-(1-decyn-9-ynylamino)benzoic acid |
| 86 | 10-octadecyn-1-ol Chem. Abst. 67, 81784s | B | p-(1-octadec-10-ynylaminio)benzoic acid |
| 87 | 1-tricosyn-1-ol Chem. Abst. 67, 81787s | B | p-(1-non-4-ynylamino)benzoic acid |
| 88 | 11-dodecyn-1-ol Chem. Abst. 68, 39015n | B | p-(1-dodec-11-ynylamino)benzoic acid |
| 89 | 11-tetradecyn-1-ol Chem. Abst. 75, 16792u | B | p-(1-tetradec-11-ynylamino)benzoic acid |
| 90 | 11-tridecyn-1-ol Chem. Abst. 75, 16792u | B | p-(1-tridec-11-ynylamino)benzoic acid |
| 91 | 16-bromo-5-hexadecyne Chem. Abst. 68, 2536g | A | p-(1-hexadec-11-ynylamino)benzoic acid |
| 92 | 12-tridecyn-1-ol Chem. Abst. 68, 39015n | B | p-(1-tridec-12-ynylamino)benzoic acid |
| 93 | 12-octadecyn-1-ol Chem. Abst. 72, 42686v | B | p-(1-octadec-12-ynylamino)benzoic acid |
| 94 | 13-tetradecyn-1-ol Chem. Abst. 68, 39015n | B | p-(1-tetradec-13-ynylamino)benzoic acid |
| 95 | 14-pentadecyn-1-ol Chem. Abst. 68, 39015n | B | p-(1-pentadec-14-ynylamino)benzoic acid |
| 96 | 5,7-octadien-4-ol Chem. Abst. 72, 42686v | B | p-(4-octa-5,7-dienylamino)benzoic acid |
| 97 | 4-ethyl-3,5-hexadecadien-2-ol Chem. Abst. 70, 20116r | B | p[2-(4-ethylhexa-3,6-dienyl)amino]benzoic acid |
| 98 | 2-methyl-4,6-heptadien-3-ol Chem. Abst. 71, 112534z | B | p-[3-(2-methylhepta-4,6-dienyl)amino benzoic acid |
| 99 | E-2,4,6-trimethyl-3,5-heptadien-2-ol | B | p-[E-2-(2,4,6-hepta-3,5-dienyl)amino]benzoic acid |
| 100 | 4,6-octadien-3-ol Chem. Abst. 69, 58770s | B | p-(1-hexa-2,4-dienylamino)benzoic acid |
| 101 | 2,4-hexadien-1-ol Chem. Abst. 67, 81787s | B | p-[1-hexa-2,4-dienylamino)benzoic acid |
| 102 | 6-isopropyl-7,7-dimethyl-3,5-octadien-2-ol Chem. Abst. 75, 36362g | B | p-[2-(6-isopropyl-7,7-dimethylocta-3,5-dienyl)amino]benzoic acid |
| 103 | 3,5,7-trimethyl-4,6-nonadien-3-ol Chem. Abst. 74, 42252s | B | p-[3-(3,5,7-trimethyl-nona-4,6-dienyl)amino]benzoic acid |
| 104 | 2,6-dimetnyl-3,5-octadien-2-ol Chem. Abst. 68, 114750d | B | p-[(2-(2,6-dimethyl-octa-3,5-dienyl)amino]benzoic acid |
| 105 | E,E-6-ethyl-4,6-decadien-3-ol Chem. Abst. 73, 130585n | B | p-[E,E-3-(6-ethyl-deca-4,6-dienyl)amino]benzoic acid |
| 106 | 5-ethyl-3,5-nonadien-2-ol | B | p-[2-(5-ethylnona-3,5-dienyl)amino]benzoic acid |

TABLE I-continued

| Example | Starting Material | Method | Product |
|---|---|---|---|
| 107 | E,E-2,4-octadien-1-ol Chem. Abst. 67, 104946n | B | p-(E,E-1-octa-2,4-dienylamino)benzoic acid |
| 108 | E,Z-2,4-nonadien-1-ol Chem. Abst. 67, 99692w | B | p-(E,Z-1-nona-2,4-dienylamino)benzoic acid |
| 109 | E,E-2,4-decadien-1-ol Chem. Abst. 67, 104946n | B | p-(E,E-1-deca-2,4-dienylamino)benzoic acid |
| 110 | E,Z-2,4-decadien-1-ol Chem. Abst. 67, 99692v. | B | p-(E,Z-1-deca-2,4-dienylamino)benzoic acid |
| 111 | E-2,5-hexadien-1-ol Chem. Abst. 73, P55709a | B | p-(E-1-hexa-2,5-dienylamino)benzoic acid |
| 112 | Z-2,5-hexadienyl-1-ol Chem. Abst. 73, P55709a | B | p-(Z-1-hexa-2,5-dienylamino)benzoic acid |
| 113 | E(+)-4-ethyl-2,5-dimethyl-2,5-hexadien-1-ol Chem. Abst. 71, 70152m | B | p-[E(+)-1-(2,5-dimethylhexa-2,5-dienyl)amino]benzoic acid |
| 114 | E-2,5,5-trimethyl-3,6-heptadien-1-ol Chem. Abst. 74, 52962n | B | p-[E-2-(2,5,5-trimethylhepta-3,6-dienyl)-amino]benzoic acid |
| 115 | Z-2,5,5-trimethyl-3,6-heptadien-1-ol Chem. Abst. 74, 52962n | B | p-[Z-2-(2,5,5,-trimethylhepta-3,6-dienyl)-amino]benzoic acid |
| 116 | Z,E-3,7-dimethyl-2,5-octadien-1-ol Chem. Abst. 71, 61565a | B | p-[Z-E-1-(3,7-dimethylocta-2,5-dienyl)amino]benzoic acid |
| 117 | E-2,6-dimethyl-2,6-heptadien-1-ol Chem. Abst. 72, 32036u | B | p-[E-1-(2,6-dimethylhepta-2,6-dienyl)amino]benzoic acid |
| 118 | E,E-2,6-octadien-1-ol | B | p-(E,E-1-octa-2,6-dienylamino)benzoic acid |
| 119 | E,E-2,6-dimethyl-2,6-octadien-1-ol Chem. Abst. 71, 2204n | B | p-[E,E-1-(2,6-dimethylocta-2,6-dienyl)amino]benzoic acid |
| 120 | Z,E-2,6-dimethyl-octadien-1-ol Chem. Abst. 71, 22204n | B | p(Z,E-1-(2,6-dimethylocta-2,6-dienylamino)benzoic acid |
| 121 | E,Z-2,6-nonadien-1-ol Chem. Abst. 72, 24504e | B | p-(E,Z-1-nona-2,6-dienylamino)benzoic acid |
| 122 | E,Z-3-ethyl-7-methyl-2,6-nonadien-1-ol Chem. Abst. 75, 63019g. | B | p-[E,Z-1-(3-ethyl-7-methylnona-2,6-dienyl)-amino]benzoic acid |
| 123 | 3,7,11,11-tetramethyl-2,6-dodecadien-1-ol Chem. Abst. 75, P117969n | B | p-[1-(3,7,11,11-tetramethyldodeca-2,6-dienyl)amino]benzoic acid |
| 124 | E,E-3,7,11-trimethyl-2,6-dodecadien-1-ol Chem. Abst. 69, 978z | B | p-[E,E-1-(3,7,11-trimethyldodeca-2,6-dienyl)amino]benzoic acid |
| 125 | E-Z-3,7,11-trimethyl-2,6-dodecadien-1-ol Chem. Abst. 69, 978g | B | p-(E,Z-1-(3,7,11-trimethyldodeca-2,6-dienyl)amino]benzoic acid |
| 126 | 2,7-octadien-1-ol Chem. Abst. 74, P41892P | B | p-(1-octa-2,7-dienylamino)benzoic acid |
| 127 | E-3,7-dimethyl-2,7-octadien-1-ol Chem. Abst. 68, 114750d | B | p[E-1-(3,7-dimethylocta-2,7-dienyl)amino]benzoic acid |
| 128 | Z,3,7-dimethyl-2,7-octadien-1-ol Chem. Abst. 68, 114750d | B | p-[Z-1-(3,7-dimethylocta-2,7-dienyl)amino]benzoic acid |
| 129 | 3,4,8-trimethyl-2,7-nonadien-1-ol | B | p-[1-(3,4,8-trimethylnona-2,7-dienyl)amino]benzoic acid |
| 130 | 3,4,8-trimethyl-2,8-nonadien-1-ol Chem. Abst. 68, 29184c | B | p-[1-(3,4,8-trimethylnona-2,8-dienyl)amino]benzoic acid |
| 131 | 2,9-decadien-1-ol Chem. Abst. 68, 68373h | B | p-(1-deca-2,9-dienylamino)benzoic acid |
| 132 | E,3,7,11-trimethyl-2,10dodecadien-1-ol Chem. Abst. 69, 978z | B | p-[E-1-(3,7,11-trimethyldodeca-2,10-dienyl)-amino]benzoic acid |
| 133 | Z-3,7,11-trimethyl-2,10-dodecadien-1-ol | B | p-[Z-1-(3,7,11-trimethyldodeca-2,10-dienyl)-amino]benzoic acid |
| 134 | E,E-4-methyl-3,5-heptadien-1-ol Chem. Abst. 66, 104730s | B | p-[E,E-1-(4-methylhepta-3,5-dienyl)amino]-benzoic acid |
| 135 | E,Z-4-methyl-3,5-heptadien-1-ol Chem. Abst. 66, 104730s | B | p-[E,Z-1-(4-methylhepta-3,5-dienyl)amino]-benzoic acid |
| 136 | Z-E-4-methyl-3,5-heptadien-1-ol Chem. Abst. 66, 104730s | B | p-[Z,E-1-(4-methylhepta-3,5-dienyl)-amino]benzoic acid |
| 137 | Z,Z-4-methyl-3,5-heptadien-1-ol Chem. Abst. 66, 104730s | B | p-[Z,Z-1-(4-methylhepta-3,5-dienyl)amino]-benzoic acid |
| 138 | E-4,6-dimethyl-3,5-heptadien-1-ol Chem. Abst. 66, 104730s | B | p-[E-1-(4,6-dimethylhepta-3,5-dienyl)amino]-benzoic acid |
| 139 | Z-4,6-dimethyl-3,5-heptadien-1-ol Chem. Abst. 66, 104730s | B | p-[Z-1-(4,6-dimethylhepta-3,5-dienylamino]-benzoic acid |
| 140 | E,Z-2,6-dimethyl-4,6-octadien-2-ol Chem. Abst. 68, 114750d | B | p-[E,Z-2-(2,6-dimethylocta-4,6-dienyl)amino]-benzoic acid |
| 141 | 1-hydroxy-3,7,11-trimethyl-2,6,10-dodecatriene | B | p-[1-(3,7,11-trimethyldodeca-2,6,10-trienyl)-amino]benzoic acid |
| 142 | 5-methyl-3,5-octadien-1-ol Chem. Abst. 69, 18519k | B | p-[1-(5-methylocta-3,5-dienyl)amino]benzoic acid |
| 143 | E-4-methyl-3,6-heptadien-1-ol Chem. Abst. 66, 104730s | B | p-[E-1-(4-methylhepta-3,6-dienyl)amino]-benzoic acid |
| 144 | Z-4-methyl-3,6-heptadien-1-ol Chem. Abst. 66, 104730s | B | p-[Z-1-(4-methylhepta-3,6-dienyl)amino]-benzoic acid |
| 145 | E(+)-2,6-dimethyl-4,7-octadien-2-ol Chem. Abst. 75, 49345d | B | p-[E(+)-2-(2,6-dimethylocta-4,7-dienyl)-amino]benzoic acid |
| 146 | Z(+)-2,6-dimethyl-4,7-octadien-2-ol Chem. Abst. 75, 49345d | B | p-[Z(+)-2-(2,6-dimethylocta-4,7-dienyl)-amino]benzoic acid |
| 147 | E-3,7-dimethyl-3,6-octadien-1-ol Chem. Abst. 67, 64554z | B | p-[E-1-(3,7-dimethylocta-3,6-dienyl)amino]-benzoic acid |
| 148 | Z-3,7-dimethyl-3,6-octadien-1-ol | B | p-[Z-1-(3,7-dimethylocta-3,6-dienyl)-amino]benzoic acid |
| 149 | E-3-methyl-3,7-octadien-1-ol Chem. Abst. 69, 65681x | B | p-[E-1-(3-methylocta-3,7-dienyl)amino]-benzoic acid |
| 150 | Z-3-methyl-3,7-octadien-1-ol Chem. Abst. 69, | B | p-[Z-1-(3-methylocta-3,7-dienyl)amino]-benzoic acid |

TABLE I-continued

| Example | Starting Material | Method | Product |
|---|---|---|---|
| | 26681x | | |
| 151 | E-2-methyl-4,8-nonadien-1-ol Chem. Abst. 73, 87253p | B | p-[Z-1-(4,6-dimethylhepta-3,5-dienyl)amino]benzoic acid |
| 152 | E-3,7-dimethyl-3,7-octadien-1-ol Chem. Abst. 69, 26681x | B | p-[E-1-(3,7-dimethylocta-3,7-dienyl)amino]benzoic acid |
| 153 | E-8-methyl-7-methylene-3-nonen-1-ol Chem. Abst. 70, 29098u | B | p-[E-1-(8-methyl-7-methylenenon-3-enyl)amino]benzoic acid |
| 154 | 2,4,9-trimethyl-4,8-decadien-1-ol Chem. Abst. 74, 99342s | B | p-[2-(2,4,9-trimethyldeca-4,8-dienyl)amino]benzoic acid |
| 155 | E-2-methyl-4,9-decadien-1-ol Chem. Abst. 73, 87254g | B | p-[E-2-(2-methyldeca-4,9-dienyl)amino]benzoic acid |
| 156 | 2,6-dimethyl-5,7-octadien-2-ol Chem. Abst. 72,37616t | B | p-[2-(2,6-dimethylocta-5,7-dienyl)amino]benzoic acid |
| 157 | E-3,7-dimethyl-4,6-octadien-1-ol Chem. Abst. 72, 121291r | B | p-[E-1-(3,7-dimethylocta-4,6-dienyl)amino]benzoic acid |
| 158 | Z-3,7-dimethyl-4,6-octadien-1-ol Chem. Abst. 72, 121291r | B | p-[Z-1-(3,7-dimethylocta-4,6-dienyl)amino]benzoic acid |
| 159 | E-4,7-octadien-1-ol Chem. Abst. 66, 28610k | B | p-(E-1-octa-4,7-dienylamino)benzoic acid |
| 160 | 5,8-nonadien-2-ol Chem. Abst. 68 28610k | B | p-(2-nona-5,8-dienylamino)benzoic acid |
| 161 | E-7-methyl-4,7-octadien-1-ol Chem. Abst. 66, 28610k | B | p-[E-1-(7-methylocta-4,7-dienyl)amino]benzoic acid |
| 162 | E-8-methyl-5,8-nonadien-2-ol Chem. Abst. 66, 28610k | B | p-[E-2-(8-methylnona-5,8-dienyl)amino]benzoic acid |
| 163 | E-6,10-dimethyl-5,9-undecadien-2-ol Chem. Abst. 73, 131152f | B | p-[E-2-(6,10-dimethylundeca-5,9-dienyl)amino]benzoic acid |
| 164 | 5,9,13-trimethyl-8,13-tetradecadien-2-ol Chem. Abst. 70, 28303v | B | p-[6-(5,9,13-trimethyltetradeca-8,12-dienyl)amino]benzoic acid |
| 165 | E-3,7,11-trimethyl-6,10-dodecadien-3-ol Chem. Abst. 69, 8333f | B | p-[E-3-(3,7,11-trimethyldodeca-6,10-dienyl)amino]benzoic acid |
| 166 | Z-3,7,11-trimethyl-6,10-dodecadien-3-ol Chem. Abst. 69, 8333f | B | p-[Z-3-(3,7,11-trimethyldodeca-6,10-dienyl)amino]benzoic acid |
| 167 | 5,9-dimethyl-4,8-decadien-1-ol Chem. Abst. 74, 112233n | B | p-[1-(5,9-dimethyldeca-4,8-dienyl)amino]benzoic acid |
| 168 | 15-methanesulfonyloxy-1,11-pentadecadiene Ref. B | B | p-(1-pentadeca-4,14-dienylamino)benzoic acid |
| 169 | 5,7-octadien-1-ol Chem. Abst. 68, 68503a | B | p-(1-octa-5,7-dienylamino)benzoic acid |
| 170 | E-3,7-dimethyl-5,7-octadien-1-ol Chem. Abst. 72, P90672j | B | p-[E-1-(3,7-dimethylocta-5,7-dienyl)amino]benzoic acid |
| 171 | 6,10-dimethyl-5,9-undecadien-1-ol Chem. Abst. 71, 50248y | B | p-[1-(6,10-dimethylundeca-5,9-dienyl)amino]benzoic acid |
| 172 | 2,6,10-trimethyl-5,9-undecadien-1-ol Chem. Abst. 71, 50243i | B | p-[1-(2,6,10-trimethylundeca-5,9-dienyl)amino]benzoic acid |
| 173 | 10-propyl-5,9-tridecadien-1-ol Chem. Abst. 68, 39028u | B | p-[1-(10-propyltrideca-5,9-dienyl)amino]benzoic acid |
| 174 | 5,13-tetradecadien-2-ol Chem. Abst. 66, 35672k | B | p-[1-tetradeca-5,13-dienylamino]benzoic acid |
| 175 | E-3,7,11-trimethyl-6,10-dodecadien-1-ol Chem. Abst. 69, 978z | B | p-[1-(3,7,11-trimethylododeca-6,10-dienyl)amino]benzoic acid |
| 176 | E-6,10,14-trimethyl-9,13-pentadecadien-2-ol Chem. Abst. 74, 53992j | B | p-[E-2-(6,10,14-trimethylylpentadeca-9,13-dienyl)amino]benzoic acid |
| 177 | Z-6,10,14-trimethyl-9,13-pentadecadien-2-ol Chem. Abst. 74, 53992j | B | p-[Z-2-(6,10,14-trimethylylpentadeca-9,13-dienyl)amino]benzoic acid |
| 178 | Z,Z-9,12-octadecadien-2-ol Chem. Abst. 68, 92804v | B | p-[1-octadeca-9,12-dienylamino]benzoic acid |
| 179 | E,Z-10,12-hexadecadien-1-ol Chem. Abst. 66, 106133y | B | p-(E,Z-1-hexadeca-10,12-dienylamino)benzoic acid |
| 180 | Z,E-10,12-hexadecadien-1-ol Chem. Abst. 66, P79564f | B | p-(Z,E-1-hexadeca-10,12-dienylamino)benzoic acid |
| 181 | 2-methyl-2,3-butadien-1-ol Chem. Abst. 71, 30229n | B | p-[1-(2-methylbuta-2,3-dienyl)amino]benzoic acid |
| 182 | 2-ethyl-2,3-butadien-1-ol Chem. Abst. 67, 53567e | B | p-[1-(2-ethylbuta-2,3-dienyl)amino]benzoic acid |
| 183 | 2,3,5-trimethyl-3,4-hexadien-2-ol Chem. Abst. 72, 131953x | B | p-[2-(2,3,5-trimethylhexa-3,4-dienyl)amino]benzoic acid |
| 184 | 3-isopropyl-2,4-dimethyl-4,5-hexadien-3-ol | B | p-[3-(2,4-dimethylhexa-4,5-dienyl)amino]benzoic acid |
| 185 | 2,5-dimethyl-3,4-hexadien-2-ol Chem. Abst. 68, 39152e | B | p-[2-(2,5-dimethylhexa-3,4-dienyl)amino]benzoic acid |
| 186 | 3,5-dimethyl-3,4-heptadien-2-ol Chem. Abst. 72, 131953x | B | p-[2-(3,5-dimethylhepta-3,4-dienyl)amino]benzoic acid |
| 187 | 2-methyl-3,4-heptadien-2-ol Chem. Abst. 71, 38219g | B | p-[2-(2-methylhepta-3,4-dienyl)amino]benzoic acid |
| 188 | 2,3,5-trimethyl-3,4-heptadien-2-ol Chem. Abst. 72, 131953x | B | p-[2-(2,3,5-trimethylhepta-3,4-dienyl)amino]benzoic acid |
| 189 | 3-t-butyl-2-methyl-3,4-octadien-2-ol Chem. Abst. 66, 75593s | B | p-[2-(3-t-butyl-2-methylocta-3,4-dienyl)amino]benzoic acid |
| 190 | 2-ethyl-2,3-heptadien-1-ol Chem. Abst. 75, 63063s | B | p-[1-(2-ethylhepta-2,3-dienyl)amino]benzoic acid |
| 191 | 2-methyl-3,4-octadien-2-ol Chem. Abst. 75, 140175q | B | p-[1-(2-methylocta-3,4-dienyl)amino]benzoic acid |
| 192 | 3-methyl-3,4-octadien-2-ol Chem. Abst. 66, 75593s | B | p-[2-(3-methylocta-3,4-dienyl)amino]benzoic acid |
| 193 | 5,6-decadien-4-ol | B | p-(4-deca-5,6-dienyl- |

TABLE I-continued

| Example | Starting Material | Method | Product |
|---|---|---|---|
| | Chem. Abst. 75, 76898t | | amino)benzoic acid |
| 194 | 2,3-dimethyl-3,4-octadien-2-ol Chem. Abst. 66, 75593s | B | p-[2-(2,3-dimethylocta-3,4-dienyl)amino]-benzoic acid |
| 195 | 4-ethyl-4,5-nonadien-3-ol Chem. Abst. 75, 63063s | B | p-[3-(4-ethylnona-4,5-dienyl)amino]-benzoic acid |
| 196 | 2-methyl-3-propyl-3,4-octadien-2-ol Chem. Abst. 66, 65592v | B | p-[2-(2-methyl-3-propylocta-3,4-dienyl)-amino]benzoic acid |
| 197 | 2-methyl-3,4-nonadine-2-ol Chem. Abst. 75, 140173g | B | p-[2-(2-methylnona-3,4-dienyl)amino]-benzoic acid |
| 198 | 2,8-dimethyl-3,4-nonadine-2-ol Chem. Abst. 71, 38219g | B | p-[2-(2,8-dimethylnona-3,4-dienyl)amino]-benzoic acid |
| 199 | 2-methyl-3,4-decadien-2-ol Chem. Abst. 75, 140173g | B | p-[2-(2-methyldeca-3,4-dienyl)amino]-benzoic acid |
| 200 | 2,9-dimethyl-3,4-decadien-2-ol | B | p-[2-(2,9-dimethyl-deca-3,4-dienyl)amino]-benzoic acid |
| 201 | 2-methyl-3,4-dodecadien-2-ol Chem. Abst. 71, 38219q | B | p-[2-(2-methyldodeca-3,4-dienyl)amino]-benzoic acid |
| 202 | 2-methyl-3,4-tridecadien-1-ol Chem. Abst. 71, 38219g | B | p-[2-(2-methyltrideca-3,4-dienyl)amino]-benzoic acid |
| 203 | 4,5-hexadien-2-ol Chem. Abst. 75, 5152j | B | p-(2-hexa-4,5-dienyl-amino)benzoic acid |
| 204 | 2-methyl-5,6 heptadien-3-ol Chem. Abst. 75, 5152j | B | p-[2-(2-methylhepta-5,6-dienyl)amino]-benzoic acid |
| 205 | 3,3-dimethyl-4,5-hexadien-2-ol Chem. Abst. 69, 8625x | B | p-[2-(3,3-dimethyl-hexa-4,5-dienyl)-amino]benzoic acid |
| 206 | 2,5-dimethyl-5,6-heptadien-3-ol Chem. Abst. 68, 86855w | B | p-[2-(2,5-dimethyl-hepta-5,6-dienyl)-amino]benzoic acid |
| 207 | 2,2,5-trimethyl-3,4-hexadien-1-ol Chem. Abst. 71, 29767g | B | p-[1-(1,2,5-trimethyl-hexa-3,4-dienyl) amino]-benzoic acid |
| 208 | (+) 2,2-dimethyl-3,4-hexadien-1-ol Chem. Abst. 68, 58831s | B | p-[1-(2,2-dimethyl-hexa-3,4-dienyl)-amino]benzoic acid |
| 209 | 3,4-hexadien-1-ol Chem. Abst. 66, 54943r | B | p-(1-hexa-3,4-dienyl-amino)benzoic acid |
| 210 | 2,2,3,5-tetramethyl-3,4-hexadien-1-ol Chem. Abst. 71, 29767g | B | p-[1-(2,2,3,5-tetra-methylhexa-3,4,-dienyl)-amino]benzoic acid |
| 211 | 3,3,6-trimethyl-4,5-octadien-2-ol Chem. Abst. 69, 86256x | B | p-[2-(3,3,6-trimethylocta-4,5-dienyl)-amino]benzoic acid |
| 212 | 2,5-dimethyl-5,6-heptadien-2-ol Chem. Abst. 69, 86256x | B | p-[2-(2,5-dimethyl-hepta-5,6-dienyl)-amino]benzoic acid |
| 213 | 4-methyl-4-penten 2-yn-1-ol | B | p-[1-(4-methylpent-4-en-2-ynyl)amino]benzoic acid |
| 214 | 2-methyl-2-penten 2-yn-1-ol | B | p-[1-(2-methylpent-2-en-4-ynyl)amino]benzoic acid |
| 215 | 5-hexen-3-yn-2-ol | B | p-(2-hex-5-en-3-ynyl-amino)benzoic acid |
| 216 | 7-octen-5-yn-4-ol | B | p-(4-oct-7-en-5-ynyl-amino)benzoic acid |
| 217 | 5-methyl-5-hexen-3-yn-2-ol | B | p-[2-(5-methylhex-5-en-3-ynyl)amino]benzoic acid |
| 218 | 2,5-dimethyl-1-nonen-3-yn-5-ol Chem. Abst. 69, 2433s | B | p-[5-(2,5-dimethylnon-1-en-3-ynyl)amino]-benzoic acid |
| 219 | E-3-decen-1-yn-5-ol Chem. Abst. 75, 35042r | B | p-(5-dec-3-en-1-ynyl-amino)benzoic acid |
| 220 | E-3-dodecen-1-yn-5-ol Chem.Abst. 75, 35042r | B | p-(5-dodec-3-en-1-ynyl-amino)benzoic acid |
| 221 | 2-methyl-5-hexen-5-yn-2-ol Chem. Abst. 66, 75760v | B | p-[2-(2-methylhex-5-en-3-ynyl)amino]-benzoic acid |
| 222 | 3-methyl-6-hepten-4-yn-3-ol Chem. Abst. 67, 113544g | B | p-[3-(3-methylhept-6-en-4-ynyl)amino]-benzoic acid |
| 223 | 5-methyl-1-nonen-3-yn-5-ol Chem. Abst. 67, 43345s | B | p-[5-(5-methylnon-1-en-3-ynyl)amino]-benzoic acid |
| 224 | 3-ethyl-6-hepten-4-yn-3-ol Chem. Abst. 71, 112202g | B | p-[3-(3-ethylhept-6-en-4-ynyl)amino]-benzoic acid |
| 225 | 5-ethyl-1-nonen-3-yn-5-ol Chem. Abst. 72, 31124j | B | p-[5-(5-ethylnon-1-en-3-ynyl)amino]-benzoic acid |
| 226 | 2,5-dimethyl-5-hexen-3-yn-2-ol Chem. Abst. 71, 112202g | B | p-[2-(2,5-dimethyl-hex-5-en-3-ynyl)amino]-benzoic acid |
| 227 | 3,6-dimethyl-6-hepten-4-yn-3-ol Chem. Abst. 69, 9688lm | B | p-[2-(2,5-dimethyl-hex-5-en-3-ynyl)amino]-benzoic acid |
| 228 | 3-ethyl-6-methyl-6-hepten-4-yn-3-ol Chem. Abst. 71, 1122026 | B | p-[3-(3-ethyl-6-methyl-hept-6-en-4-ynyl)amino]-benzoic acid |
| 229 | 5-ethyl-2-methyl-3-yn-5-ol Chem. Abst. 69, 2433s | B | p-[5-(5-ethyl-2-methyl-n-1-en-3-ynyl)amino]-benzoic acid |
| 230 | 2-hexen-4-yn-1-ol Chem. Abst. 68, 77868a | B | p-(1-hex-2-en-4-ynyl-amino)benzoic acid |
| 231 | 4-methyl-4-hexen-2-yn-1-ol Chem. Abst. 66, 115247r | B | p-[1-(4-methylhex-4-en-2-ynyl)amino]benzoic acid |
| 232 | 5-hexen-2-yn-1-ol Chem. Abst. 71, 80580t | B | p-(1-hex-5-en-2-ynyl-amino)benzoic acid |
| 233 | 5-methyl-5-hexen-2-yn-1-ol Chem. Abst. 70, 28152v | B | p-[1(5-methylhex-5-en-2-ynyl) amino]benzoic acid |
| 234 | 5-hexen-3-yn-1-ol Chem. Abst. 73, 109833g | B | p-(1-hex-5-en-3-ynyl-amino)benzoic acid |
| 235 | E-4-methyl-5-yn-1-ol Chem. Abst. 66, 104730s | B | p-[E-1-(4-methylhept-3-en-5-ynyl)amino]-benzoic acid |
| 236 | Z-4-methyl-5-yn-1-ol Chem. Abst. 66, 104730s | B | p-[Z-1-(4-methylhept-3-en-5-ynyl)amino]-benzoic acid |
| 237 | 3-hexen-5-yn-2-ol Chem. Abst. 75, 5152j | B | p-(2-hex-3-en-5-ynyl-amino)benzoic acid |
| 238 | 6-methyl-6-hepten-4-yn-2-ol | B | p-[2-(6-methylhept-6-en-4-ynyl)amino]-benzoic acid |
| 239 | 7-methyl-7-octen-5-yn-3-ol | B | p-[3-(7-methyloct-7-en-5-ynyl)amino]-benzoic acid |
| 240 | 2,5-dimethyl-5-hex-en-3-yn-2-ol | B | p-[2-(2-dimethylhex-5-en-3-ynyl)amino]-benzoic acid |
| 241 | 3-methyl-6-octen-4-yn-3-ol Chem. Abst. 74, 41795j | B | p-[3-(3-methyloct-6-en-4-ynyl)amino]-benzoic acid |
| 242 | 5-methyl-9-decen-6-yn-5-ol Chem. Abst. 73, 125271c | B | p-[5-(5-methyldec-9-en-6-ynyl)amino]-benzoic acid |

TABLE I-continued

| Example | Starting Material | Method | Product |
|---|---|---|---|
| 243 | 2,5,5,6-tetramethyl-6-hepten-3-yn-2-ol Chem. Abst. 70, 10801w | B | p-[2-(2,5,5,6-tetramethylhept-6-en-3-ynyl)amino]benzoic acid |
| 244 | 3-ethyl-7-octen-4-yn-3-ol Chem. Abst. 73, 3762t | B | p-[3-(3-ethyloct-7-en-4-ynyl)amino]benzoic acid |
| 245 | 3-methyl-7-octen-4-yn-3-ol Chem. Abst. 73, 3762t | B | p-[3-(3-methyloct-7-en-4-ynyl)amino)]benzoic acid |
| 246 | 2,6-dimethyl-6-hepten-3-yn-2-ol Chem. Abst. 73, 55677p | B | p-[2-(2,6-dimethylhept-6-en-3-ynyl)amino]benzoic acid |
| 247 | 3,6-diethyl-6-octen-4-yn-3-ol Chem. Abst. 68, 104850x | B | p-[3-(3,6-diethyloct-6-en-4-ynyl)amino]benzoic acid |
| 248 | 6-ethyl-6-octen-4-yn-2-ol Chem. Abst. 73, 19632z | B | p-[2-(6-ethyloct-6-en-4-ynyl)amino]benzoic]acid |
| 249 | 6-methyl-6-hepten-2-yn-1-ol Chem. Abst. 72, 3587u | B | p-[1-(6-methylhept-6-en-2-ynyl)amino]benzoic acid |
| 250 | E-4-methyl-3-hepten-6-yn-1-ol Chem. Abst. 66, 104730s | B | p-[E-1-(4-methylhept-3-en-4-ynyl)amino]benzoic acid |
| 251 | Z-4-methyl-3-hepten-6-yn-1-ol Chem. Abst. 66, 104730s | B | p-[Z-1-(4-methylhept-3-en-6-ynyl)amino]benzoic acid |
| 252 | E-2-octen-6-yn-1-ol Chem. Abst. 75, 63019g | B | p-(E-1-oct-2-en-6-ynylamino)benzoic acid |
| 253 | Z-7 methyl-6-nonen-2-yn-1-ol Chem. Abst. 70, 78718j | B | p-[Z-1-(7-methylnon-6-en-2-ynyl)amino]benzoic acid |
| 254 | 8-methyl-7-methylene-3-nonyn-1-ol Chem. Abst. 66, 29098u | B | p-[1-(8-methyl-1-methylenenon-3-ynyl)amino]benzoic acid |
| 255 | E-2-decen-4-yn-1-ol Chem. Abst. 67, 99692v | B | p-(1-dec-2-en-4-ynylamino)benzoic acid |
| 256 | 4-methy-4-decen-8-yn-1-ol Chem. Abst. 75, 110510x | B | p-[1-(4-methyldec-4-en-8-ynyl)amino]benzoic acid |
| 257 | E-2-undecen-4-yn-1-ol. Chem. Abst. 66, 28594h | B | p-(1-undec-2-en-4-ynylamino)benzoic acid |
| 258 | 6-methyl-5-undecen-2-yn-1-ol Chem. Abst. 71, P101399h | B | p-[1-(6-methylundec-5-en-2-ynyl)amino]benzoic acid |
| 259 | E-5-tetradecen-3-yn-1-ol Chem. Abst. 73, 87370z | B | p-(E-1-tetradec-5-en-3-ynylamino)benzoic acid |
| 260 | Z-5-tetradecen-3-yn-1-ol Chem. Abst. 73, 87370z | B | p-(Z-1-tetradec-5-en-3-ynylamino)benzoic acid |
| 261 | 10-propyl-9-tridecen-5-yn--ol Chem. Abst. 72, 12017k | B | p-[1-(10-propyltridec-9-en-5-ynyl)amino]benzoic acid |
| 262 | 17-octdecen-14-yn-1-ol Chem. Abst. 68, 39015n | B | p-(1-octadec-17-en-14-ynylamino)benzoic acid |
| 263 | 2,4-dimethyl-1,4-hexadien-3-ol Chem. Abst. 74, 87269u | B | p-[3-(2,4-dimethylhexa-1,4-dienyl)amino]benzoic acid |
| 264 | 1,5-hexadien-3-ol Chem. Abst. 73, 44822f | B | p-(3-hexa-1,5-dienylamino)benzoic acid |
| 265 | 3,5-dimethyl-1,5-hexadien-3-ol Chem. Abst. 67, 53415d | B | p-[3-(3,5-dimethylhexa-1,5-dienyl)amino]benzoic acid |
| 266 | 2,6-dimethyl-1,6-heptadien-3-ol Chem. Abst. 73, 87490p | B | p-[3-(2,6-dimethylhepta-1,6-dienyl)amino]benzoic acid |
| 267 | E-2,6-dimethyl-1,6-octadien-3-ol Chem. Abst. 71, 61565a | B | P-[E-3-(2,6-dimethylocta-1,6-dienyl)amino]benzoic acid |
| 268 | Z-2,6-dimethyl-1,6 octadien-3-ol Chem. Abst. 71, 61565a | B | p-[Z-3-(2,6-dimethylocta-1,6-dienyl)amino]benzoic acid |
| 269 | 3-ethyl-7-methyl-1,6-octadien-3-ol Chem. Abst. 66, P76192x | B | p-[3-(3-ethyl-7-methylocta-1,6-dienyl)amino]benzoic acid |
| 270 | 3-t-butyl-7-methyl-1,6-octadien-3-ol Chem. Abst. 66, P76192x | B | p-'-(3-1-butyl-7-methylocta-1,6-dienyl)amino]benzoic acid |
| 271 | 7,9-dimethyl-1,6-decadien-3-ol Chem. Abst. 71, P60078c | B | p-[3-(7,9-dimethyldeca-1,6-dienyl)amino]benzoic acid |
| 272 | 3,7-dimethyl-1,6-decadien-3-ol Chem. Abst. 67, 2688n | B | p-[3-(3,7-dimethyldeca-1,6-dienyl)amino]benzoic acid |
| 273 | 2-methyl-1,5-heptadien-4-ol Chem. Abst. 67, 53415d | B | p-[4-(2-methylhepta-1,5-dienyl)amino]benzoic acid |
| 274 | 4,6-dimethyl-1,5-heptadien-4-ol Chem. Abst. 67, 53415d | B | p-[4-(4,6-dimethylhepta-1,5-dienyl)amino]benzoic acid |
| 275 | E,E-3,4,5-trimethyl-2,5-heptadien-4-ol Chem. Abst. 72, 2823f | B | p-[E,E-4-(3,4,5-trimethylhepta-2,5-dienyl)amino]benzoic acid |
| 276 | E,Z-3,4,5-trimethyl-2,5-heptadien-4-ol Chem. Abst. 72, 2823f | B | p-[E,Z-4-(3,4,5-trimethylhepta-2,5-dienyl)amino]benzoic acid |
| 277 | Z,Z-3,4,5-trimethyl-2,5-heptadien-4-ol Chem. Abst. 72, 2823f | B | p-[Z,Z-4-(3,4,5-trimethylhepta-2,5-dienyl)amino]benzoic acid |
| 278 | 2-methyl-2,9-decadien-5-ol Chem. Abst. 73, 87254q | B | p-[5-(2-methyldeca-2,9-dienyl)amino]benzoic acid |
| 279 | 8-methyl-1,7-nonadien-5-ol Chem. Abst. 73, 87253p | B | p-[5-(8-methylnona-1,7-dienyl)amino]benzoic acid |
| 280 | 3,4,7,7-tetramethyl-1,5-octadien-4-ol Chem. Abst. 67, 63514z | B | p-[5-(3,4,7,7-tetramethylocta-1,5-dienyl)-amino]benzoic acid |
| 281 | 3,4-dimethylene-2-hexanol Chem. Abst. 69, 106850s | B | p-[2-(3,4-dimethylenehexyl)amino]benzoic acid |
| 282 | 3-methyl-2-methylene-3-butene-1-ol Chem. Abst. 74, 42503z | B | p-[1-(3-methyl-2-methylenebut-3-enyl)amino]benzoic acid |
| 283 | 2-methylene-3-butene-1-ol Chem. Abst. 73, P67478n | B | p-[1-(2-methylenebut-3-enyl)amino]benozoic acid |
| 284 | 3,3-dimethyl-2-methylene-4-penten-1-ol Chem. Abst. 74, 52962n | B | p-[1-(3,3-dimethyl-2-methylenepent-4-enyl)-amino]benzoic acid |
| 285 | 2-methylene-3-methyl-4-hexen-1-ol Chem. Abst. 68, 59021q | B | p-[1-(2-methylene-3-methylhex-4-enyl)-amino]benzoic acid |
| 286 | 2,4-dimethyl-3-methylene-5-hexen-2-ol Chem. Abst. 72, 66299x | B | p-[2-(2,4-dimethyl-3-methylenehex-5-enyl)-amino]benzoic acid |
| 287 | 2,4,4-trimethyl-3-methylene-5-hexen-2-ol Chem. Abst. 74, 52962n | B | p-[2-(2,4,4-trimethyl-3-methylenehex-5-enyl)amino]benzoic acid |
| 288 | E-2-methyl-3-methyl- | B | p-[E-2-(2-methyl-3- |

TABLE I-continued

| Example | Starting Material | Method | Product |
|---|---|---|---|
| | ene-5-hepten-2-ol Chem. Abst. 72, 132999d | | methylenehept-5-enyl)-amino]benzoic acid |
| 289 | Z-2-methyl-3-methylene-5-hepten-2-ol Chem. Abst. 72, 132999d | B | p-[Z-2-(2-methyl-3-methylenehept-5-enyl)amino]benzoic acid |
| 290 | 2,6-dimethyl-1,3-methylene-5-hepten-2-ol Chem. Abst. 72, 132999d | B | p-[2-(2,6-dimethyl-3-methylenehept-5-enyl)amino]benzoic acid |
| 291 | 3,7-dimethyl-2-methylene-6-octen-1-ol Chem. Abst. 68, 114750d | B | p-[1-(3,7-dimethyl-2-methyleneoct-6-enyl)-amino]benzoic acid |
| 292 | 3,7-dimethyl-2-methylene-7-octen-1-ol Chem. Abst. 70, P37191j | B | p-[1-(3,7-dimethyl-2-methyleneoct-7-enyl)-amino]benzoic acid |
| 293 | 3-isopropylidene-2,5-dimethyl-4-hexen-2-ol Chem. Abst. 74, 53105x | B | p-[2-(3-isopropylidene-2,5-dimethylhex-4-enyl)amino]benzoic acid |
| 294 | 2-methyl-6-methylene-7-octen-4-ol Chem. Abst. 69, 10548y | B | p-[4-(2-methyl-6-methyleneoct-7-enyl) amino]-benzoic acid |
| 295 | 2-isopropylidene-5-methyl-4-hexene-1-ol Chem. Abst. 72, 32299d | B | p-[1-(2-isopropylidene-5-methylhex-4-enyl)-amino]benzoic acid |
| 296 | 7-methyl-3-methylene-6-octen-1-ol Chem. Abst. 73, 131140a | B | p-[1-(7-methyl-3-methyleneoct-6-enyl)amino]-benzoic acid |
| 297 | 2-methyl-6-methylene-7-octen-2-ol Chem. Abst. 71, P61600h | B | p-[2-(2-methyl-6-methyleneoct-7-enyl)amino]-benzoic acid |
| 298 | E-2-ethylidene-6-methyl-5-hepten-1-ol Chem. Abst. 68, 114750d | B | p-[E-1-(2-ethylidene-6-methylhept-5-enyl)amino]-benzoic acid |
| 299 | Z-2-ethylidene-6-methyl-5-hepten-1-ol Chem. Abst. 68, 114750d | B | p-[Z-1-(2-ethylidene-6-methylhept-5-enyl)amino]-benzoic acid |
| 300 | 2,5-dimethyl-3-vinyl-4-hexen-2-ol Chem. Abst. 69, 45983p | B | p-[2-(2,5-dimethyl-3-vinylhex-4-enyl)amino]-benzoic acid |
| 301 | 2-isopropenyl-5-methyl-4-hexen-1-ol Chem. Abst. 68, 111190k | B | p-[1-(2-isopropenyl-5-methylhex-4-enyl)amino]-benzoic acid |
| 302 | 2-vinyl-5-hepten-1-ol Chem. Abst. 75, P151673w | | p-[1-(2-vinylhept-5-enyl)amino]benzoic acid |
| 303 | 2-vinyl-6-hepten-1-ol Chem. Abst. 75, P151673w | | p-[1-(2-vinylhept-6-enyl)amino]benzoic acid |
| 304 | 2-(2-methylpropenyl)-5-hexen-1-ol Chem. Abst. 68, 114750d | B | p-[1-(2-methylpropenylhex-5-enyl)amino]benzoic acid |
| 305 | 7-methyl-3-vinyl-6-octen--ol Chem. Abst. 66, p115838j | B | P-[1-(7-methyl-3-vinyloct-6-enyl)amino]-benzoic acid |
| 306 | 2-allyl-4-methyl-4-penten-1-ol Chem. Abst. 72, 21731r | B | p-[1-(2-allyl-4-methyl-pent-4-enyl)amino]-benzoic acid |
| 307 | 3-methyl-5-undecen-1-yn-3-ol Chem. Abst. 71, P101399h | B | p-[-(3-methylundec-5-en-1-ynyl)amino]benzoic acid |
| 308 | 3,4,8-trimethyl-8-nonen-1-yn-3-ol Chem. Abst. 68, 29184r | B | p-[3-(3,4,8-trimethyl-non-8-en-1-ynyl)amino]-benzoic acid |
| 309 | 1-dodecen-4-yn-3-ol Chem. Abst. 66, 75603v | B | p-(3-dodec-1-en-4-ynyl amino)benzoic acid |
| 310 | 11-dodecen-1-yn-3-ol Chem. Abst. 73, 120015n | B | p-(3-dodec-11-en-1-ynyl amino)benzoic acid |
| 311 | 1-undecen-5-yn-4-ol Chem. Abst. 69, 2432r | B | p-(4-undec-1-en-5-ynyl amino)benzoic acid |
| 312 | 3,7-dimethyl-6-nonen-1-yn-3-ol Chem. Abst. 71, P91265v | B | p-[3-(3,7-dimethylnon-6-en-1-ynyl)amino]-benzoic acid |
| 313 | 7,7-dimethyl-1-nonen-8-yn-5-ol Chem. Abst. 74, 22939t | B | p-[5-(7,7-dimethylnon-1-en-8-ynyl)amino]-benzoic acid |
| 314 | 2,3-dimethyl-1-nonen-4-yn-3-ol Chem. Abst. 68, 39161g | B | p-[3-(2,5-dimethylnon-1-en-4-ynyl)amino]-benzoic acid |
| 315 | 3,7-dimethyl-7-octen-1-yn-3-ol Chem. Abst. 73, P7095a | B | p-[3-(3,7-dimethyloct-7-en-1-ynyl)amino]-benzoic acid |
| 316 | 4,6-dimethyl-5-hepten-1-yn-4-ol Chem. Abst. 66, 95156e | B | p-[3-(4,6-dimethylhept-5-en-1-ynyl)amino]-benzoic acid |
| 317 | 1-penten-4-yn-3-ol Chem. Abst. 74, P140935m | B | p-(3-pent-1-en-4-ynyl amino)benzoic acid |

EXAMPLE 318

Preparation of 4-(pentadec-4-enylamino)benzhydroxamic acid

To a suspension of 4-(pentadec-4-enylamino)benzoic acid (44 g.) in glyme (350 ml.) and pyridine (70 ml.) at 0° C. is added trifluoroacetic anhydride (67 ml., 100 g.) at such a rate as to maintain the temperature at 20°–30° C. The resulting solution is stirred at 10°–15° C. for 2 hours, then diluted with ether (400 ml.), cooled in an ice-bath and ice (100 gm.) is added. The mixture is stirred vigorously at ambient temperature for 1 hour. The aqueous layer is extracted with ether and the combined ether extracts are washed with water, brine, dried over sodium sulfate and concentrated in vacuo to provide 57 g. of 4-[N-trifluoroacetyl-N-(pentadec-4-enyl)amino]benzoic acid as an oil that solidifies upon standing.

The N-trifluoroacetyl derivative (57 g.) is dissolved in thionyl chloride (300 ml.) and refluxed for 3 hours. After cooling, the mixture is diluted with toluene and concentrated in vacuo. The residue is diluted again with hot toluene and filtered. The toluene is concentrated in vacuo to provide 61 g. of 4-[N-trifluoroacetyl-N-(pentadec-4-enyl)-amino]benzoyl chloride as an oil.

To a stirred solution of hydroxylamine hydrochoride (16 g.) in pyridine (75 ml.) and dichloromethane (35 ml.) is added dropwise the previously prepared benzoyl chloride derivative (11.5 g.) in dichloromethane (20 ml.). After 1 hour, the mixture is diluted with water and extracted with ether. The combined organic extract is washed with 5% hydrochloric acid until the aqueous wash remains acidic. The ether extract is then washed with water, brine, dried with sodium sulfate and concentrated in vacuo to afford 4-[N-trifluoroacetyl-N-(pentadec-4-enyl)amino]benzhydroxamic acid as an oil.

A portion of this oil (0.9 g.) is dissolved in ethanol (20 ml.), 1 N sodium hydroxide solution is added, and the mixture is stirred at ambient temperature. The mixture is stirred at ambient temperature. The mixture is chilled and filtered to provide a white solid that is washed with ethanol. The white solid is recrystallized from hot ethanol to provide 4-(pentadec-4-enylamino)benzhydroxamic acid.

EXAMPLE 319

Preparation of esters

Treatment of the acids of Examples 1–317 and 327–365 with trifluoroacetic anhydride to provide the N-COCF$_3$ derivative, followed by treatment with thionyl chloride to provide the N-COCF$_3$ acid chloride, followed by treatment with one of the following alcohols, followed by removal of the N-COCF$_3$ group with sodium hydroxide by the method of Example 318 provides the corresponding ester of the starting acid.

Alcohols: methanol, ethanol, 2-methoxyethanol, butanol, pentanol, cyclopentanol, cyclohexanol, 1,2-propanediol, 1,3-propanediol, ethylene glycol, glycerol, glycidol, methyl glycolate, ethyl glycolate, glycolic acid, 2-hydroxypropionic acid, 3-hydroxybutyric acid, 4-hydroxybutyric acid, glyceric acid, 3-diethylamino-1-propanol, 1-diethylamino-2-propanol, 3-dimethylamino-1-propanol, 2-diisopropylaminoethanol, 3-(4-methyl-1-piperazino)-1,2-propanediol, 3-methoxy-1,2-propanediol, N-piperidineethanol, N,N-diethylethanolamine, benzyl alcohol, p-fluorobenzyl alcohol, p-bromobenzyl alcohol, p-chlorobenzyl alcohol, p-methoxybenzyl alcohol, m-chlorobenzyl alcohol, p-carboxybenzyl alcohol, phenyl, p-fluorophenol, p-bromophenol, p-chlorophenol, p-methoxyphenol, p-carboxyphenol, 4-cyanophenol, 3-hydroxypyridine, 2-chloro-3-hydroxypyridine, 5-carboxy-3-hydroxypyridine.

EXAMPLE 320

Preparation of amides

Treatment of the acids of Examples 1–317 and 327–365 with trifluoroacetic anhydride to provide the N—COCF$_3$ derivative, followed by treatment with thionyl chloride to provide the N—COCF$_3$ acid chloride, followed by treatment with one of the amines of the list below, followed by removal of the N—COCF$_3$ group with sodium hydroxide by the method of Example 318 provides the corresponding amides of the starting acid.

Amines: β-alanine, allylamine, allylcyclohexylamine, aminoacetonitrile, α-aminoacetophenone, 2-amino-1-butanol, 3-aminobutyric acid, 4-aminobutyric acid, 1-amino-1-cyclopentanemethanol, 2-amino-5-diethylaminopentane, N-(2-aminoethyl)morpholine, N-(2-aminoethyl)piperazine, N-(2-aminoethyl)piperidine, 2-amino-2-ethyl-1,3-propanediol, 2-(2-aminoethyl)pyridine, N-(2-aminoethyl)pyrrolidine, DL-4-amino-3-hydroxybutyric acid, 5-aminolevulinic acid, aminomethanesulfonic acid, p-aminomethylbenzenesulfonamide, 2-amino-3-methyl-1-butanol, aminomethylcyclobutane, 4-(amino-methyl)cyclohexanecarbonitrile, 1-aminomethyl-1-cyclohexanol, aminomethylcyclopropane, 4-(aminomethyl)piperidine, 2-amino-2-methyl-1,3-propanediol, 2-amino-2-methyl-1-propanol, 2-(aminomethyl)-2-propanol, 2-aminomethylpyridine, 3-aminomethylpyridine, 4-aminomethylpyridine, 2-amino-1-phenylethanol, 2-amino-3-phenyl-1-propanol, 3-amino-3-phenylpropionic acid, 3-amino-1,2-propanediol, 1-amino-2-propanol, N-(3-aminopropyl)diethanolamine, N-(3-aminopropyl)morpholine, 1-(3-aminopropyl)-2-pipecoline, N-(3-aminopropyl)-2-pyrrolidinone, 5-aminovaleric acid, bis-(2-ethanolethyl)amine, bis-(2-methylallyl)amine, p-bromophenethylamine, 3-bromopropylamine hydrobromide, n-butylamine, sec-butylamine, tert-butylamine, 2-chlorobenzylamine, 3-chlorobenzylamine, 5-chlorobenzylamine, 2-chloroethylamine, 3-chloropropylamine, cyclobutylamine, cycloheptylamine, 1,3-cyclohexanebis(methylamine), cyclohexanemethylamine, cyclohexylamine, cyclopentylamine, cyclopropylamine, 3-(di-n-butylamino)propylamine, 1,5-dimethylhexylamine, α,4-dimethyl-3-hydroxyphenethylamine, 1,1-dimethylpropargylamine, 1,2-dimethylpropylamine, 1,2-diphenylethylamine, ethylamine, ethyl-3-aminobutyrate, ethyl-4-aminobutyrate, 2-(ethylamino)ethanol, 1-ethylpropylamine, 1-ethynylcyclohexylamine, m-fluorobenzylamine, p-fluorobenzylamine, 2-fluoroethylamine, furfurylamine, n-heptylamine, isoamylamine, isopropylamine, m-methoxybenzylamine, p-methoxybenzylamine, 2-methoxyethylamine, o-methoxyphenethylamine, p-methoxyphenethylamine, N-methyl-β-alaninenitrile, 2-methylallylamine, methylamine, methylaminoacetonitrile, 2-(methylamino)ethanol, 2-methylbenzylamine, 3-methylbenzylamine, 4-methylbenzylamine, 1-methylbutylamine, 4-methylcyclohexylamine, 1-norepinephrine, 4-phenylbutylamine, 1-phenylcyclopropanemethylamine, trans-2-phenylcyclopropylamine, D(−)-α-phenylglycinol, 2-phenylglycinonitrile, phenylpropanolamine, 3-phenyl-1-propylamine, monopropargylamine, propylamine, taurine, tetrahydrofurfurylamine, 1,2,3,4-tetrahydro-1-naphthylamine, 2-(p-tolyl)ethylamine, m-aminobenzoic acid, p-aminobenzoic acid, o-aminobenzyl alcohol, p-aminobenzyl alcohol, 3,5-dimethylpiperidine, 2-ethylpiperidine, 3-hydroxypiperidine, 4-hydroxypiperidine, 2-iminopiperidine, isonipecotamide, isonipecotic acid, methyl-4-oxo-3-piperidinecarboxylate, 2-methylpiperidine, 3-methylpiperidine, 4-methylpiperidine, nipecotamide, 4-phenylpiperidine, 4-phenyl-1,2,3,5-tetrahydropyridine, pipecolinic acid, piperidine, 2-piperidineethanol, 2-piperidinemethanol, 3-piperidinemethanol, 4-piperidinopiperidine, 4-piperidone, 1,2,3,6-tetrahydropyridine, 2,2,6,6-tetramethylpiperidine, 2,2,6,6-tetramethyl-4-piperidinol, 2,2,6,6-tetramethyl-4-piperidone, 4,4-trimethylenedipiperidine, 2-methylpiperidine, 3-methylpiperidine, 4-methylpiperidine, 4-phenylpiperidine, piperidine, morpholine, hexamethyleneimine, heptamethyleneimine, pentamethyleneimine, pyrrolidine, N-methylpiperazine, dl-alanine, hydrazine, N-acetylhydrazine, dl-valine, Δ$^3$-piperidine, dl-leucine, 2-aminoisobutyric acid.

EXAMPLE 321

Preparation of N-[4-(9-Octadecenylamino)benzoyl]benzamide

Sodium hydride (1.0 g., 50% dispersion in mineral oil) is washed with hexane three times under nitrogen. To the dry sodium hydride is added 5 ml. of freshly distilled tetrahydrofuran. To this suspension is added a solution of 2.4 g. of benzamide in 5 ml. of tetrahydrofuran. After complete reaction (30 min.), a solution of 0.9 g. 4-[N-trifluoroacetyl-N-(9-octadecenyl)amino]benzoyl chloride (Example 318) in 3 ml. of tetrahydrofuran is added. After stirring at ambient temperature for 1 hour, the reaction mixture is poured into water and extracted twice with ether. The ether extracts are washed with water, brine, dried with sodium sulfate, and concentrated in vacuo. The residue is recrystallized from ether-acetonitrile (1:1) to provide N-{4-[N-trifluoroacetyl-N-(9-octadecenyl)amino]benzoyl}benzamide.

The N-trifluoroacetyl compound is in turn treated with ethanol and 1 N sodium hydroxide and the mixture is stirred at ambient temperature for 6 hours. Chilling and filtration affords a white solid which is recrystallized from ethanol to yield N-[4-(9-octadecenylamino)-benzoyl]benzamide.

EXAMPLE 322

Preparation of N-[4-(substituted amino)benzoyl]benzamides

Treatment of the N-COCF$_3$ acid halides (prepared by the method of Example 318 from the corresponding acids of Examples 1–317 and 327–365) with benzamide and sodium hydride followed by removal of the N—COCF$_3$ group by the method of Example 321 is productive of the corresponding benzamides.

EXAMPLE 323

Preparation of p-(4-pentadecenylamino)-N-(phenylsulfonyl)benzamide

A solution of 31.4 g. of benzenesulfonamide in 250 ml. of dry dimethylacetamide is added dropwise, with stirring and cooling, to a suspension of 5.5 g. of sodium hydride in 100 ml. of dry dimethylacetamide over 30 minutes at room temperature. Stirring is continued for a further 30 minutes. In the meantime, a mixture of 36.2 g. of 4-(4-pentadecenylamino)benzoic acid in 1200 ml. of methylene chloride, 300 ml. of dimethoxyethane, and 40 ml. of thionyl chloride is refluxed for 1 hour and 15 minutes. The solution is evaporated to an oil which is co-evaporated twice with added dioxane to remove excess thionyl chloride. To the resulting oily residue of 4-(4-pentadecenylamino)benzoyl chloride hydrochloride is added, in one portion, the previously prepared mixture of sodium benzenesulfonamide in dimethylacetamide. The mixture is stirred for 30 minutes, without cooling, and is then filtered through a bed of diatomaceous earth. The filtrate is poured into 2 l. of water, and 250 ml. of saturated sodium chloride solution is added to coagulate the precipitate. The mixture is filtered and the product is washed with water and partially air dried. The product is dissolved in methylene chloride, the mixture is filtered through diatomaceous earth, and brine is added to break the emulsion. The layers are separated, the organic phase is dried over anhydrous sodium sulfate and filtered through a bed of 300 g. of hydrous magnesium silicate. The product is eluted with an additional 3 l. of methylene chloride. The first approximately 1 l. of filtrate is set aside and the remainder is evaporated to dryness. The residue is crystallized three times from toluene and the product is dried in the Abderhalden at 65° C. to provide the title compound as colorless crystals.

EXAMPLE 324

Preparation of p-(substituted amino)-N-(sulfonyl)benzamides

Treatment of the acid chloride hydrochloride (prepared from the corresponding carboxylic acids of Examples 1–317 and 327–365 by the procedure of Example 366) with the following sulfonamides by the procedure of Example 323 is productive of the corresponding p-(substituted amino)-N-(sulfonyl)benzamide. The sulfonamide starting materials are benzenesulfonamide, methanesulfonamide, p-methylphenylsulfonamide, p-nitrophenylsulfonamide, p-chlorophenylsulfonamide.

EXAMPLE 325

Preparation of methyl esters

Treatment of the p-(substituted amino)benzoic acids of Examples 1–317 and 327–365 with excess diazomethane is productive of the corresponding methyl ester.

EXAMPLE 326

Preparation of hexyl esters

Treatment of the p-(substituted amino)benzoic acids of Examples 1–317 and 327–365 with excess diazohexane is productive of the corresponding hexyl esters.

EXAMPLE 327

Preparation of p-[1-(2,3-methano)octylamino]benzoic acid

To a stirred mixture of 5 g. of zinc-copper couple prepared by the Shank-Shechter Method [R. S. Shank and H. Shechter, J. Org. Chem., 24, 1825 (1959)], 0.02 g. of iodine, and 100 ml. of anhydrous ether is added 8.7 g. (0.05 mol) of methylene iodide. The mixture is heated in the absence of atmospheric moisture until a spontaneous reaction begins as evidenced by continued refluxing of the ether when the heat source is removed. Upon completion of the exothermic reaction, the mixture is refluxed for 30 minutes, the heat is removed and to this mixture is added a solution of 5.4 g. (0.04 mol) of cis-2-octenol [L. P. Paquette and R. F. Eizember, J. Am. Chem. Soc., 91, 7110 (1969)] in 10 ml. of anhydrous ether at a rate sufficient to maintain constant reflux. When the addition is complete, the mixture is refluxed for 3 hours. The flask is cooled and the mixture is filtered and the filtrate is washed with cold dilute hydrochloric acid and saturated sodium bicarbonate, dried and evaporated to give Z-1-hydroxymethyl-2-n-pentyl-cyclopropane.

Preparation of the tosylate by the method of Example 2, followed by condensation with ethyl p-aminobenzoate by the method of Example 2, followed by saponification by the method of Example 2 provides p-[1-(2,3-methano)octylamino]benzoic acid.

EXAMPLE 328

Treatment of the indicated olefin of the table with Zinc and diiodomethane by the method of Example 327 to produce the corresponding cyclopropyl compound followed by treatment of the halide with ethyl-p-aminobenzoate by the method of Example 1, followed by saponification of the resulting ester by the method of Example 1, is productive of the p-(methano-alkyl)amino benzoic acid of Table II (Method C).

Treatment of the olefinic alcohols of Table II with Zinc and diiodomethane by the method of Example 327 will produce the corresponding cyclopropyl alkanols which upon treatment with methanesulfonic anhydride (Method of Example 2) will produce the corresponding methanesulfonate ester which upon treatment with ethyl p-aminobenzoate by the procedure of Example 2 followed by saponification will produce the p-(methano-alkyl)aminobenzoic acids of Table II (Method D).

TABLE II

| Example | Starting Material | Method | Product |
|---|---|---|---|
| 328 | 3-bromo-3-isopropyl-4-methyl-1-pentene Chem. Abst. 54, 4355a | C | p-[3-(3-isopropyl-4-methyl-1,2-methanopentyl)-amino]benzoic acid |
| 329 | 4-bromo-2-heptene Chem. Abst. 70, 67482x | C | p-[4-(2,3-methanoheptyl)-amino]benzoic acid |
| 330 | 4-bromo-2,4-dimethyl-2-hexene Chem. Abst. 70, 3169t | C | p-[4-(2,4-dimethyl-2,3-methanohexyl)amino]-benzoic acid |
| 331 | 5-chloro-3,5-dimethyl-3-heptene Chem. Abst. 54, 1256e | C | p-[5-(3,5-dimethyl-3,4-methanoheptyl)amino]-benzoic acid |
| 332 | Z-1-hydroxy-2-hexadecene Ref. B | D | p-[Z-1-(2,3-methanohexadecyl)amino]benzoic acid |
| 333 | E-1-hydroxy-2-hexadecene Ref. B | D | p-[E-1-(2,3-methanohexadecyl)amino]benzoic acid |
| 334 | 1-bromo-4-methyl-3-heptene Chem. Abst. 71, 102020q | C | p-[1-(4-methyl-3,4-methanoheptyl)amino]-benzoic acid |
| 335 | 1-bromo-4-methyl-3-heptene Chem. Abst. 71, P101399h | C | p-[1-(4-methyl-3,4-methanononyl)amino]-benzoic acid |
| 336 | E-7-bromo-3-heptene Chem. Abst. 74, 99419f | C | p-(E-1-(4,5-methanoheptyl)amino]benzoic acid |
| 337 | 1-bromo-5,9-dimethyl-4-decene Chem. Abst. 51, 8699g | C | p-[1-(5,9-dimethyl-4,5-methanodecyl)-amino]benzoic acid |
| 338 | 1-methanesulfonyloxy-4-tetradecene Ref. B | C | p-[1-(4,5-methanotetradecyl)amino]-benzoic acid |
| 339 | 1-methanesulfonyloxy-4-hexadecene Ref. B | C | p-[1-(4,5-methanohexadecyl)amino]-benzoic acid |
| 340 | 6-bromo-1-hexene Chem. Abst. 66, 2142j | C | p-[1-(5,6-methanohexyl)-amino]benzoic acid |
| 341 | 6-bromo-2-methyl-1-hexene Chem. Abst. 75, 109624f | C | p-[1-(5,6-methano-5-methylhexyl)amino]benzoic acid |
| 342 | 6-chloro-1-heptene Chem. Abst. 72, 31877g | C | p-[2-(6,7-methanoheptyl)-amino]benzoic acid |
| 343 | 6-bromo-2-methyl-2-heptene Chem. Abst. 54, 13166f | C | p-[2-(5,6-methano-6-methylheptyl)amino]benzoic acid |
| 344 | 7-chloro-2-octene Chem. Abst. 75, 129245m | C | p-[2-(6,7-methanooctyl)-amino]benzoic acid |
| 345 | E-1-chloro-4-nonene Chem. Abst. 67, 32294y | C | p-[E-1-(4,5-methanononyl)-amino]benzoic acid |
| 346 | 7-bromo-1-heptene | C | p-[1-(6,7-methanoheptyl)-amino]benzoic acid |
| 347 | 7-chloro-1-octene Chem. Abst. 75, 129245m | C | p-[2-(7,8-methanooctyl)-amino]benzoic acid |
| 348 | 6-bromo-6-methyl-1-heptene Chem. Abst. 66, 94482w | C | p-[1-(2-methyl-6,7-methanoheptyl)amino]-benzoic acid |
| 349 | 6-chloro-2-methyl-1-heptene Chem. Abst. 75, 129245 | C | p-[1-(6-methyl-6,7-methanoheptyl)amino]-benzoic acid |
| 350 | E-8-bromo-2-octene Chem. Abst. 74, 99419f | C | p-[1-(6,7-methanooctyl)-amino]benzoic acid |
| 351 | 8-bromo-2,6-dimethyl-2-octene Chem. Abst. 72, 90573c | C | p-[1-(3,7-dimethyl-6,7-methanooctyl)amino]-benzoic acid |
| 352 | 11-bromo-5-undecene Chem. Abst. 67, 73101b | C | p-[1-(6,7-methanoundecyl)amino]benzoic acid |
| 353 | 8-bromo-1-octene Chem. Abst. 70, 10990g | C | p-[1-(7,8-methanooctyl)-amino]benzoic acid |
| 354 | R-8-iodo-7-methyl-1-octene Chem. Abst. 74, 12573e | C | p-[1-(2-methyl-7,8-methanooctyl)amino]-benzoic acid |
| 355 | 1-chloro-7-tetradecene Chem. Abst. 54, 22461h | C | p-[1-(7,8-methanotetradecyl)amino]benzoic acid |
| 356 | 9-chloro-1-nonene Chem. Abst. 70, 114490k | C | p-[1-8,9-methanononyl)-amino]benzoic acid |
| 357 | 1-bromo-8-heptadecene Chem. Abst. 52, 249d | C | p-1-(8,9-methanoheptadecyl)amino]benzoic acid |
| 358 | E-1-bromo-9-octadecene Chem. Abst. 70, 46779j | C | p-E-1-(9,10-methano-octadecyl)amino]benzoic acid |
| 359 | Z-1-bromo-9-octadecene Chem. Abst. 70, 46779j | C | p-Z-1-(9,10-methanooctadecyl)amino]benzoic acid |
| 360 | 11-chloro-1-undecene Chem. Abst. 66, P19046d | C | p-1-(10,11-methanoundecyl)amino]benzoic acid |
| 361 | 12-iodo-3,7,11-trimethyl-1-dodecene | C | p-1-(2,6,10-trimethyl-11,12-methanododecyl)-amino]benzoic acid |
| 362 | 13-bromo-1-tridecene Chem. Abst. 67, 43348v | C | p-1-(12,13-methanotridecyl)amino]benzoic acid |
| 363 | 22-bromo-9-docosene Chem. Abst. 73, 44976j | C | p-1-(13,14-methanodocosyl)amino]benzoic acid |
| 364 | 16-methanesulfonyloxy-1-hexadecene Ref. B | C | p-1-(15,16-methanohexadecyl)amino]benzoic acid |
| 365 | 3-chloro-2,4,4-trimethyl-1-pentene Chem. Abst. 72, 1110811 | C | p-3-(2,4,4-trimethyl-1,2-methanopentyl)amino]-benzoic acid |

EXAMPLE 366

Preparation of 4-(4-tetradecenylamino)benzoyl chloride

A cold solution of 25 g. of 4-(4-tetradecenylamino)-benzoic acid in 500 ml. dimethoxyethane-methylene chloride (4:1) is prepared and dry hydrochloric acid is bubbled through the solution until no more precipitate forms.

The solution is treated with 25 ml. thionyl chloride and refluxed until all of the precipitate has dissolved. The solvents are evaporated to yield an orange, semi-crystalline mass.

EXAMPLE 367

Preparation of N-trifluoroacetyl-4-(4-tetradecenylamino)-benzoyl chloride

To a stirred, ice-cold suspension of 9 g. (24.9 m moles) 4-(4-tetradecenylamino)benzoic acid in 100 ml. dimethoxy ethane and 16 ml. pyridine is treated with 18 ml. trifluoroacetic anhydride. The solution is stirred at 0° C. for 30 minutes at room temperature. The solution is diluted with 300 ml. ether and 100 g. ice. After stirring vigorously for 15 minutes, the phases are separated, the ether solution is washed with brine, dried and evaporated to a white amorphous solid.

To 9.2 g. of the above product in 30 ml. methylene chloride and 0.5 ml. dimethylformamide is added 5.7 ml. thionyl chloride. After 20 hours at reflux, the solvents are evaporated to yield the product as a light yellow, mobile oil.

EXAMPLE 368

Preparation of
O-[4-(4-tetradecenylamino)benzoyl]malic acid

A warm solution of N-carbobenzyloxy-4-(4-tetradecenylamino)benzoyl chloride and 1.3 g. triethylamine in 100 ml. ether is treated with 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% palladium-on-carbon at 20 psi until hydrogen uptake stops. The catalyst is filtered, the solution is evaporated, and the residue is crystallized from acetic acid to yield the title compound as a tan, crystalline mass.

EXAMPLE 369

Preparation of diethyl
O-[4-(4-tetradecenylamino)benzoyl]malate

In a manner similar to Example 368, a solution of 6.0 g. N-carbobenzyloxy-4-(4-tetradecenylamino)benzoyl chloride and 1.2 g. triethylamine in 100 ml warm ether is treated with 2.3 g. diethylmalate. After one hour at reflux, the precipitate is filtered off and washed with warm ether. After evaporation to dryness the residue is dissolved in 50 ml. 30% hydrobromic in acetic acid and warmed at 50° C. for 2 hours. The solvents are evaporated and the product is partitioned between methylene chloride and water. The layers are separated and the methylene chloride layer is evaporated. The residue is crystallized from acetone to yield the product as colorless crystals.

EXAMPLE 370

Preparation of diethyl
O-[4-(4-tetradecenylamino)benzoyl]tartrate

N-trifluoroacetyl-4-(4-tetradecenylamino)benzoyl chloride and 1.2 g. triethylamine in 100 ml. warm ether is treated with 2.5 g. diethyl tartrate and refluxed for 24 hours. The hot solution is filtered, the residue is washed with hot ether, and the solvent evaporated from the combined filtrate and washings to yield a solid residue. After dissolving in aqueous methanolic potassium carbonate, the product is precipitated by acidification, filtered, and dried. Crystallization from acetone yields the diethyl tartrate as a white, crystalline solid.

EXAMPLE 371

Preparation of
1-[4-(N-t-butyloxycarbonyl-4-tetradecenylamino)benzoyl]imidazole

To a solution of 10 g. 4-(4-tetradecenylamino)benzoic acid in 100 ml. dioxane is treated with 4.0 g. t-butylazidoformate and 10 ml. pyridine. After stirring at room temperature for 18 hours, the protected amidoacid is precipitated from solution by addition of 150 ml. water. The product is collected and thoroughly dried. The crude product is dissolved in 200 ml. of a mixture consisting of methylene chloride/dimethoxyethane/pyridine (1:4:1), and to this is added 5.4 g. 1,1'-carbonyldiimidazole. The solution is stirred overnight at room temperature and the solvents are evaporated to yield the title compound as a thick, orange oil.

EXAMPLE 372

2,3-Dihydroxypropyl 4-(4-pentadecenyl)benzoate

A solution of 7.35 g. of 4-(4-pentadecenyl)benzoic acid in 50 ml. of hexamethylphosphoramide is treated with 4.80 g. of 25% aqueous sodium hydroxide followed by 11.0 g. of 3-chloro-1,2-propanediol and then is heated at 140° C. for 6 hours. The mixture is diluted with water and ether and filtered to yield a white solid. Recrystallization from acetonitrile and then from carbon tetrachloride affords the product as a white solid.

EXAMPLE 373

2,3-Dihydroxypropyl 4-(4-tetradecenylamino)benzoate

A mixture of 2.25 g. of methyl 4-(4-tetradecenylamino)benzoate, 280 mg. of glycerol, and 1.37 g. of p-toluenesulfonic acid is heated at 180° C. for 18 hours and then is partitioned between ether and 3% aqueous sodium carbonate solution. The ether layer is separated, dried, and evaporated to yield the product as a white solid.

EXAMPLE 374

2,3-Dihydroxypropyl 4-(4-tetradecenylamino)benzoate

A solution of 11.8 g. of 4-(4-tetradecenylamino)benzoic acid, 1.00 g. of glycerol, and 5.35 ml. of boron trifluoride etherate in 200 ml. of toluene is stirred under reflux for 48 hours. The solution is treated with an additional 5.35 ml. of boron trifluoride etherate and refluxing is continued for 120 hours. Dilution with water and methylene chloride followed by filtration affords the benzoate as a white solid.

EXAMPLE 375

Preparation of
N-[4-(4-tetradecenylamino)benzoyl]alanine

A solution of 4.75 g. of N-trifluoroacetyl-4-(tetradecenylamino)benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the solvent is evaporated from the combined filtrate and washings. After treatment of the residue with aqueous methanolic potassium carbonate, the product is precipitated by acidification, filtered, and dried. Crystallization from acetone yields the product as a white, crystalline solid.

EXAMPLE 376

Preparation of
1-{4-(N-t-butyloxycarbonyl)-N-(4-tetradecenylamino)-benzoyl}imidazole A solution of 10 g. of 4-(4-tetradecenylamino)benzoic acid in 100 ml. dioxane is treated with 4.0 g. of t-butylazidoformate and 10 ml. pyridine. After stirring at room temperature for 18 hours, the protected amidoacid is precipitated from solution by addition of 150 ml. of water. The product is collected and thoroughly dried. The crude product is dissolved in 200 ml. of a mixture consisting of methylene chloride/dimethoxy ethane/pyridine (1:4:1), and to this is added 5.4 g. of 1,1'-carbonyldiimidazole. The solution is stirred overnight at room temperature and the solvents are evaporated to yield the title compound as a thick orange oil.

EXAMPLE 377

Preparation of 2-(ethoxycarbonyl)vinyl 4-(4-tetradecenylamino)benzoate

To a mixture containing 4.3 g. 1-[4-(N-t-butyloxycarbonylamino)benzoyl]imidazole, 50 ml. chloroform, and 50 ml. 5N sodium hydroxide is added 3 g. ethyl α-formyl acetate. The mixture is vigorously stirred for 24 hours. The layers are separated, and the chloroform solution is washed once with 50 ml. 1N sodium hydroxide. The solvent is evaporated from the chloroform layer and the residue is heated for 30 minutes at 40° C. in 50 ml. anhydrous trifluoroacetic acid. The solvent is again evaporated and the oil is crystallized from acetone to yield the product as light yellow crystals.

EXAMPLE 378

Preparation of N-carbobenzyloxy-4-(4,14-pentadecadienylamino)benzoyl chloride

To 15 g. of 4-(4,14-pentadecadienylamino)benzoic acid in 200 mml. warm chloroform is added 15 g. sodium carbonate in 150 ml. water. To the vigorously stirred mixture is added 10 g. carbobenzoyl chloride. After 2 hours stirring at 40° C., the layers are separated, the chloroform layer is washed three times with 1N hydrochloric acid, dried, and the solvent evaporated to yield an oil. The oil is dissolved in 300 ml. toluene, treated with 15 ml. of thionyl chloride, and the solution is refluxed for 5 hours. The solvents are evaporated and the residue is dissolved three times in toluene, evaporating each time to yield a viscous, orange oil.

EXAMPLE 379

Preparation of 1-[4-(4,14-pentadecadienylamino)benzoyl]piperidine

To a warm solution of 4-[N-carbobenzoyloxy-4,14-pentadecadienylamino)benzoyl chloride and 1.3 g. of triethylamine in 100 ml. ether is added 1.2 g. of piperidine. An immediate precipitate forms, but the mixture is refluxed for one hour and filtered while hot. The solid is washed several times with hot ether, then the ether is evaporated from the combined filtrate and washings to yield a white solid. The product is dissolved in tetrahydrofuran (100 ml.) and hydrogenated over 600 mg. 10% palladium on carbon at 20 psi until hydrogen uptake stops. The catalyst is filtered. The solution is evaporated, and the residue is crystallized from acetic acid to yield the title compound as a crystalline mass.

EXAMPLE 380

Preparation of 1-[4-(4,14-pentadecadienylamino)benzoyl]pyrrolidine

A solution of 6.0 g. of 4-[N-carbobenzoyloxy-N-(4,14-pentadecadienylamino)]benzoyl chloride and 1.2 g. triethylamine in 100 ml. warm ether is treated with 1.1 g. of pyrrolidine. After 1 hour at reflux, the precipitate is filtered off and washed with warm ether. After evaporation of the combined filtrate and washings to dryness, the residue is dissolved in 50 ml. 30% hydrobromine in acetic acid and warmed at 50° for 2 hours. The solvents are evaporated and the product is partitioned between methylene chloride and water. The layers are separated and the methylene chloride is evaporated. The residue is crystallized from acetone to yield colorless crystals.

EXAMPLE 381

Preparation of O-[4-(4,14-pentadecadienylamino)benzoyl]malic acid

To a warm solution of N-carbobenzyloxy-4-(4,14-pentadecadienylamino)benzoyl chloride and 1.3 g. triethylamine in 100 ml. ether is treated with 2 g. malic acid. An immediate precipitate forms, but the mixture is refluxed for one hour and filtered while hot. The solid is wahsed several times with hot ether, then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered. The solution is evaporated and the residue is crystallized from acetic acid to yield the title compound as white crystals.

EXAMPLE 382

Preparation of N-[4-(4-tetradecenylamino)benzoyl]alanine

A solution of 4.75 g. of N-trifluoroacetyl-4-(4-tetradecenylamino)benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the combined filtrate and washings are evaporated. After treatment of the residue with aqueous methanolic potassium carbonate, the product is precipitated by acidification, filtered, and dried. Crystallization from acetone yields the product a white, crystalline solid.

EXAMPLE 383

Preparation of 4-chlorophenyl 4-(4-tetradecenylamino)benzoate

To a solution of 6.4 g. 4-chlorophenol and 7.6 g. triethylamine in 500 ml. methylene chloride is added 10.4 g. 4(4-tetradecenylamino)benzoyl chloride hydrochloride in 250 ml. methylene chloride. After four hours at reflux, the solution is cooled, washed with water and dilute phosphoric acid, and dried. After passing the solution through a column of alumina, the solvent is evaporated and the residue is crystallized from diisopropyl ether.

EXAMPLE 384

Preparation of N-[4-(4-tetradecenylamino)benzoyl]-2-amino ethanesulfonic acid

To a stirred solution of 2.50 g. of taurine and 5.6 ml. of triethylamine in 22.5 ml. of water is added 5.55 g. of N-{p-[2,2,2-trifluoro-N-(4-tetradecenyl)acetamido]benzoyloxy}succinimide as a solution in 45 ml. of ethanol. After 24 hour, the mixture is treated with 20 ml. of 2.0M sodium hydroxide and 25 ml. of water. After stirring for 10 minutes, the mixture is acidified with dilute hydrochloric acid, and the crude product is collected by filtration. Recrystallization affords the title compound as a white solid.

EXAMPLE 385

Preparation of 3-[4-(4-pentadecenylamino)benzoyl]-4-carboethoxythiazolidine

One-tenth mole of 4-(4-pentadecenylamino)benzoyl chloride hydrochloride in methylene chloride is added to a solution of 0.1 mole of ethyl thiazolidine-4-carboxylate in chloroform containing two equivalents of triethylamine. After 5 hours at 20° C. the solution is filtered and evaporated to a white solid which is recrystallized from acetonitrile.

EXAMPLE 386

Preparation of 3-[4-(4-pentadecenylamino)benzoyl]-4-carboxythiazolidine

By means of the alkaline hydrolysis method of Example 2 the ethyl ester of Example 385 is converted to the subject carboxylic acid. This acid is also prepared using the procedure of Example 385 except that the acylation of the thiazolidine-4-carboxylic acid is carried out in aqueous acetone sodium bicarbonate solution.

EXAMPLE 387

Preparation of N-[4-(4-pentadecenylamino)benzoyl]glycine

A mixture of 26.4 g. of ethyl N-[4-(4-pentadecenylamino)benzoyl]glycinate, 110 ml. of 1 N sodium hydroxide solution, and 100 ml. of ethanol is stirred at ambient temperature for 2 hours and then partially evaporated. The gaseous solution is washed with diethyl ether, acidified with 6 N hydrochloric acid, and filtered. The white solid is dried in vacuo and recrystallized from acetone.

EXAMPLE 388

Preparation of N-[4-(4-pentadecenylamino)benzoyl]-2,3-di-hydroxypropylamine

To a mixture containing 4.3 g. of [N-(t-butyloxycarbonyl)-4-(4-pentadecenylamino)benzoyl]imidazole, 50 ml. of chloroform, and 50 ml. of 5 N sodium hydroxide is added 1.1 g. of 3-amino-1,2-propanediol. The mixture is vigorously stirred for 24 hours, the layers are separated, and the chloroform solution is washed once with 50 ml. of 1 N sodium hydroxide. The solvent is evaporated and the residue is heated for 30 minutes at 40° C. in 50 ml. of anhydrous trifluoroacetic acid. The solvent is again evaporated and the resulting oil is crystallized from acetone to yield the product as light yellow crystals.

EXAMPLE 389

Preparation of N-(3-bromopropyl)-4-(4-tetradecenylamino)benzamide

To a slurry of 21.80 g. of 3-bromopropylamine hydrobromide in 200 ml. of glyme at 3° C. is added a solution of 23.9 g. of 4-(4-tetradecenylamino)benzoyl chloride hydrochloride in 65 ml. of glyme, concurrently with 26 ml. of triethylamine diluted to 39 ml. with 1,2-dimethoxyethane. The solution is warmed to reflux and 0.2 g. of 4-dimethylaminopyridine is added. The solution was heated for four hours and cooled overnight. The solid is removed and the mother liquor diluted with 200 ml. of water to yield a solid which is crystallized from cyclohexane and recrystallized from acetonitrile to yield the product.

EXAMPLE 390

Preparation of 2-[4-(4-tetradecenylamino)phenyl[-5,6-dihydro-[4H]-1,3-oxazine

To 0.4 g. of sodium hydride in 100 ml. of 1,2-dimethoxyethane is added 2.14 g. of N-(3-bromopropyl)-4-(4-tetradecenylamino)benzamide and 12 ml. of triethylamine. The turbid solution is heated to reflux for 20 hours. The solution is diluted with 100 ml. of water and cooled overnight. The solid is collected, washed with water, crystallized from cyclohexane, and recrystallized from acetonitrile to yield the product.

EXAMPLE 391

Preparation of 2-[4-(4-tetradecenylamino)phenyl]oxazoline

To a slurry of 15 g. of 2-bromoethylamine hydrobromide in 150 ml. of 1,2-dimethoxyethane are added simultaneously solutions of 31 g. of 4-(4-tetradecenylamino)benzoyl chloride hydrochloride in 60 ml. of 1,2-dimethoxyethane and 50 cc. of triethylamine (dropwise). Upon addition of 0.5 g. of 4-dimethylaminopyridine the mixture is stirred at room temperature overnight. The solution is refluxed for one hour and filtered. The solid is oven dried and partitioned between methylene chloride and water. The layers are separated and the organic phase dried over magnesium sulfate. The organic layer is concentrated and the residue collected and crystallized from cyclohexane and recrystallized from acetonitrile to yield the product.

EXAMPLE 392

Preparation of tetrahydropyranyl 4-(4-tetradecenylamino)benzoate

A mixture of 7 g. 4-(4-tetradecenylamino)benzoic acid, 2 g. dihydropyran and 100 mg. of anhydrous p-toluenesulfonic acid in 50 ml. toluene is stirred at room temperature for 20 hours. The solution is washed with saturated sodium bicarbonate, dried, and evaporated. The residue is collected and crystallized from methylcyclohexane to yield the product as white crystals.

EXAMPLE 393

Preparation of pyridin-3-yl 4-(4-tetradecenylamino)benzoate

A 6 g. sample of 4-(4-tetradecenylamino)benzoic acid and 2.7 g. 1,1'-carbonyldiimidazole in 50 ml. dry tetrahydrofuran is stirred for 2 hours. Then, 1.58 g. 3-hydroxypyridine and a trace of sodium hydride catalyst is added and the reaction is refluxed for 3 hours. The solution is cooled, filtered, and evaporated. The product is crystallized from isopropanol.

I claim:

1. A compound of the formula:

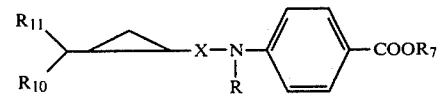

wherein $R_7$ is hydrogen, or a loweralkyl group; $R_{11}$ is hydrogen or a $C_1$ to $C_{15}$ alkyl group unsubstituted or substituted with at least one methyl group; $R_{10}$ is hydrogen methyl; X is a bond or a $C_1$ to $C_{15}$ branched or unbranched alkylene group unsubstituted or substituted with at least one methyl group; and R is selected from the group consisting of hydrogen or methyl and the pharmaceutically acceptable non-toxic acid-addition and cationic salts thereof.

2. A compound according to claim 1 wherein $R_{10}$ is hydrogen.

3. A compound according to claim 2 wherein $R_{11}$ is hydrogen.

4. A compound according to claim 2 wherein X is a bond.

5. A compound according to claim 2 wherein $R_{11}$ is hydrogen and X is a $C_{10}$ to $C_{15}$ unbranched alkylene group.

6. A compound according to claim 2 wherein $R_{11}$ is a $C_{10}$ to $C_{15}$ alkyl group and X is a bond.

* * * * *

UNITED STATES PATENT OFFICE
CERTIFICATE OF CORRECTION

Patent No. 4,230,878   Dated October 28, 1980

Inventor(s) Robert Gordon Shepherd

It is certified that error appears in the above-identified patent and that said Letters Patent are hereby corrected as shown below:

Claim 1, line 4 after the word hydrogen insert the word -- or --.

Signed and Sealed this

Fourteenth Day of April 1981

[SEAL]

Attest:

RENE D. TEGTMEYER

Attesting Officer   Acting Commissioner of Patents and Trademarks